US011491114B2

(12) United States Patent
Javeri et al.

(10) Patent No.: US 11,491,114 B2
(45) Date of Patent: Nov. 8, 2022

(54) FORMULATIONS FOR ENTERIC DELIVERY OF THERAPEUTIC AGENTS

(71) Applicant: CuriOralRx, Wilmington, MA (US)

(72) Inventors: Indu Javeri, North Andover, MA (US); Kaliappanadar Nellaiappan, Lexington, MA (US)

(73) Assignee: CuriOralRx, LLC, Wilmington, MA (US)

( * ) Notice: Subject to any disclaimer, the term of this patent is extended or adjusted under 35 U.S.C. 154(b) by 0 days.

(21) Appl. No.: 15/291,480

(22) Filed: Oct. 12, 2016

(65) Prior Publication Data

US 2018/0098946 A1 Apr. 12, 2018

(51) Int. Cl.
| | | |
|---|---|---|
| *A61K 9/51* | (2006.01) | |
| *A61K 38/28* | (2006.01) | |
| *C07K 16/32* | (2006.01) | |
| *C07K 16/24* | (2006.01) | |
| *C07K 16/28* | (2006.01) | |
| *C07K 16/10* | (2006.01) | |
| *A61K 9/00* | (2006.01) | |
| *A61K 9/19* | (2006.01) | |
| *A61K 39/395* | (2006.01) | |

(52) U.S. Cl.
CPC .......... *A61K 9/5161* (2013.01); *A61K 9/5138* (2013.01); *A61K 38/28* (2013.01); *A61K 39/39591* (2013.01); *C07K 16/1027* (2013.01); *C07K 16/241* (2013.01); *C07K 16/248* (2013.01); *C07K 16/2863* (2013.01); *C07K 16/32* (2013.01); *A61K 9/0095* (2013.01); *A61K 9/19* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,579,730 A | | 4/1986 | Kidron et al. |
| 4,724,148 A | * | 2/1988 | Sonobe ................ A61K 9/1617 424/480 |
| 5,609,871 A | | 3/1997 | Michael et al. |
| 5,620,708 A | | 4/1997 | Amkraut et al. |
| 5,641,515 A | | 6/1997 | Ramtoola |
| 5,916,595 A | * | 6/1999 | Chen .................... A61K 9/0004 424/480 |
| 6,036,978 A | | 3/2000 | Gombotz et al. |
| 6,630,171 B1 | * | 10/2003 | Huille ..................... A61K 8/88 424/130.1 |
| 6,881,421 B1 | | 4/2005 | da Silveira et al. |
| 7,282,194 B2 | | 10/2007 | Sung et al. |
| 7,291,598 B2 | | 11/2007 | Sung et al. |
| 7,541,028 B2 | | 6/2009 | Sung et al. |
| 8,673,359 B2 | | 3/2014 | Cho et al. |
| 8,859,004 B2 | | 10/2014 | Zhang et al. |
| 9,101,547 B2 | | 8/2015 | Qian et al. |
| 2003/0095928 A1 | | 5/2003 | McGurk et al. |
| 2004/0224019 A1 | | 11/2004 | Shefer et al. |
| 2005/0170004 A1 | | 8/2005 | Rosenberger et al. |
| 2005/0181059 A1 | * | 8/2005 | Jacob ...................... A61K 9/14 424/489 |
| 2006/0018826 A1 | * | 1/2006 | Unger ................... A61K 9/0019 424/1.11 |
| 2007/0087957 A1 | | 4/2007 | Kidron |
| 2008/0107749 A1 | | 5/2008 | Maitra et al. |
| 2008/0241260 A1 | * | 10/2008 | Devarajan ............... A61K 9/006 514/1.1 |
| 2009/0098205 A1 | | 4/2009 | Sharma et al. |
| 2010/0004157 A1 | | 1/2010 | Mani et al. |
| 2010/0021549 A1 | | 1/2010 | Meyrueix et al. |
| 2011/0189299 A1 | * | 8/2011 | Okubo .................. A61K 9/0043 424/491 |
| 2013/0034589 A1 | | 2/2013 | Zhang et al. |
| 2013/0034602 A1 | | 2/2013 | Qian et al. |
| 2014/0120164 A1 | | 5/2014 | Fischer et al. |
| 2014/0199296 A1 | * | 7/2014 | Bannister ............ A61K 31/7068 424/133.1 |

(Continued)

FOREIGN PATENT DOCUMENTS

| | | |
|---|---|---|
| EP | 1429731 | 3/2003 |
| WO | 2010/113177 A2 | 10/2010 |

(Continued)

OTHER PUBLICATIONS

Matrix Definition [online]. Merriam-Webster, 2/22/2108 [retrieved on Feb. 22, 2018]. Retrieved from the internet: <www.merriam-webster.com/dictionary/matrix>.*
Sciencing Website [online], Chris Deziel. Jan. 2017 [retrieved on Jun. 3, 2019], Retrieved from the internet: <https://sciencing.com/general-characteristics-acids-bases-7166371.html>. (Year: 2017).*
Licciardi et al. Molecular Pharmaceutics vol. 10, pp. 1644-1654. (Year: 2013).*
Devarajan and Sonavane. Drug Development and Industrial Pharmacy vol. 33, pp. 101-111. (Year: 2007).*
Brange et al. Acta Pharm Nord. 4(3): 149-158. (abstract only) (Year: 1992).*
Khan et al. Drug Development and Industrial Pharmacy, 26(5): 549-554. (Year: 2000).*
M. Alai, et al., "Application of polymeric nanoparticles and micelles in insulin oral delivery", Journal of Food and Drug Analysis, (2015), vol. 23, pp. 351-358.

(Continued)

*Primary Examiner* — Katherine Peebles
(74) *Attorney, Agent, or Firm* — Verrill Dana, LLP

(57) ABSTRACT

Formulations containing pH-sensitive nanoparticles for the enteric delivery of therapeutic agents are provided. The nanoparticles include a pH-sensitive polymer that protects the therapeutic agent against degradation in the stomach and allows it to be released in the small intestine or colon. The nanoparticle formulation is particularly effective at protecting sensitive biotherapeutic agents from degradation when administered orally, and makes it possible to avoid administration of such agents by injection. Also provided are methods for producing the formulations, as well as methods of treating diseases employing the formulations.

24 Claims, 17 Drawing Sheets

(56) References Cited

U.S. PATENT DOCUMENTS

| | | | |
|---|---|---|---|
| 2014/0199379 A1* | 7/2014 | Tartour | A61K 39/0011 424/450 |
| 2014/0342004 A1 | 11/2014 | Aprikyan et al. | |
| 2015/0017229 A1 | 1/2015 | Hamidi | |
| 2016/0206741 A1 | 7/2016 | Knipe et al. | |

FOREIGN PATENT DOCUMENTS

| | | |
|---|---|---|
| WO | 2012170547 | 12/2012 |
| WO | 2013160773 | 10/2013 |

OTHER PUBLICATIONS

T. Yoshida, et al., "pH- and ion-sensitive polymers for drug delivery", Expert Opin. Drug Deliv., Nov. 2013, vol. 10, No. 11, pp. 1497-1513.

A. Elsayed, "Oral Delivery of Insulin: Novel Approaches", Recent Advances in Novel Drug Carrier Systems, 2012, pp. 281-314.

A. Ahmad, et al., "Oral Nano-Insulin Therapy: Current Progress on Nanoparticle-Based Devices for Intestinal Epithelium-Targeted Insulin Delivery", J. Nanomedic. Nanotechnol., (2012), S4:007, 10 pgs.

R. Kumar, et al., "Eudragit Polymers in Colon Targeted Oral Delivery of Insulin", International Journal of Pharmaceutical, Chemical and Biological Sciences, (2014), vol. 4, No. 4, pp. 968-979.

M. Desai, et al., "Gastrointestinal uptake of biodegradable microparticles: effect of particle size", Pharm. Res., Dec. 1996, vol. 13, No. 12, pp. 1838-1845 (Abstract).

D. Kaklotar, et al., "Transition from passive to active targeting of oral insulin nanomedicines: enhancement in bioavailability and glycemic control in diabetes", Nanomedicine (London), (2016), vol. 11, No. 11, pp. 1465-1486.

P. Finotelli, et al., "Microcapsules of alginate/chitosan containing magnetic nanoparticles for controlled release of insulin", Colloids Surf. B. Biointerfaces, Nov. 1, 2010, vol. 81, No. 1, pp. 206-211 (Abstract).

M. Niu, et al., "Hypoglycemic activity and oral bioavailability of insulin-loaded liposomes containing bile salts in rats: the effect of cholate type, particle size and administered dose", Eur. J. Pharm. Biopharm., Jun. 2012, vol. 81, No. 2, pp. 265-272 (Abstract).

M. Li, et al., Preparation and characterization of insulin nanoparticles employing chitosan and poly (methylmethacrylate/methylmethacrylic acid) copolymer, J. Nanosci. Nanotechnol., Sep.-Oct. 2006, vol. 6, Nos. 9-10, pp. 2874-2876 (Abstract).

S. Vino, et al. "pH Responsive Casein Microparticles as a Carrier for Methotrexate", International Journal of Pharmaceutical Sciences and Research, (2011), vol. 2, No. 2, pp. 383-390.

A. Delgado, et al., "PLG microparticles stabilised using enteric coating polymers as oral vaccine delivery systems", Vaccine, (1999), vol. 17, pp. 2927-2938.

A. Jouyban, et al. "Review of Pharmaceutical Applications of N-Methyl-2-Pyrrolidone", J. Pharm. Pharmaceut. Sci., (2010), vol. 13, No. 4, pp. 524-535.

P. Kam, et al., "Mucoadhesive liposomal delivery systems: the choice of coating material", Drug Development and Industrial Pharmacy, (2011), vol. 37, No. 4, pp. 482-488.

K Animesh, et al., "Applicability and Approaches of (Meth) Acrylate Copolymers (Eudragits) in Novel Drug Delivery Systems", Current Drug Therapy, (2012), vol. 7, pp. 219-234.

M. Avadi, et al., "Preparation and characterization of insulin nanoparticles using chitosan and Arabic gum with ionic gelation method", Nanomedicine: Nanotechnology, Biology, and Medicine, (2010), vol. 6, pp. 58-63.

P. Fonte, et al., "Oral Insulin Delivery: How Far Are We?", Journal of Diabetes Science and Technology, Mar. 2013, vol. 7, Issue 2, pp. 520-531.

V. Agarwal, et al., "Current Status of the Oral Delivery of Insulin", Pharmaceutical Technology, Oct. 2001, pp. 76-90.

E. Marais, et al., "Eudragit L100/N-Trimethylchitosan Chloride Microspheres for Oral Insulin Delivery", Molecules, (2013), vol. 18, pp. 6734-6747.

K Gradauer, et al., "Chemical coupling of thiolated chitosan to preformed liposomes improves mucoadhesive properties". International Journal of Nanomedicine, (2012), vol. 7, pp. 2523-2534.

M. Sharma, et al., "Development of enteric submicron particle formulation of papain for oral delivery", International Journal of Nanomedicine, (2011), vol. 6, pp. 2097-2111.

R. Kumar, et al., "Eudragit Coated Microparticulate Delivery of Bovine Insulin for Oral Delivery", International Journal of Research in Pharmacy and Chemistry, (2014), vol. 4, No. 3, pp. 698-712.

V. Nikam, et al., "Eudragit A Versatile Polymer: A Review", Pharmacologyonlilne, (2011), vol. 1., pp. 152-164.

Voltan R et al. Preparation and Characterization of Innovative Protein-coated Poly(Methylmethacrylate) Core-shell Nanoparticles for Vaccine Purposes. Pharm Res. Oct. 2007, vol. 24, Issue 10, pp. 1870-1882.

Zabihi et al. PLGA-HPMC nanoparticles prepared by a modified supercritical anti-solvent technique for the controlled Yelease of insulin. The Journal of Supercritical Fluids. vol. 99, Apr. 2015, pp. 15-22.

Viehof et al. Oral insulin delivery in rats by nanoparticles prepared with non-toxic solvents. International Journal of Pharmaceutics 443 (2013) 169-174.

Chatuverdi. Oral insulin delivery using deoxycholic acid conjugated PEGylated polyhydroxybutyrate co-polymeric nanoparticles. Nanomedicine. 10.10 (May 2015): p. 1569.

Sajeesh et al. Novel pH responsive polymethacrylic acid-chitosan-polyethylene glycol nanoparticles for oral peptide delivery. J Biomed Mater Res B Appl Biomater. Feb. 2006;76(2):298-305.

Sajeesh et al. Cyclodextrin-insulin complex encapsulated polymethacrylic acid based nanoparticles for oral insulin delivery. Int J Pharm. Nov. 15, 2006;325(1-2):147-54.

Foss et al. Development of acrylic-based copolymers for oral insulin delivery. Eur J Pharm Biopharm. Mar. 2004;57 K2):163-9.

Liu et al. Efficient mucus permeation and tight junction opening by dissociable "mucus-inert" agent coated trimethyl chitosan nanoparticles for oral insulin delivery. Journal of Controlled Release 222 (2016) 67-77.

Nakamura et al. Key functions in polymer carriers for intestinal absorption of insulin. Int J Pharm. Apr. 16, 2008; 354 (1-2): 135-142.

Gibco Human Neural Stem Cell Manual, Dec. 7, 2009, 32 pgs.

V. C. Bond, et al., "Poly-L-Ornithine-Mediated Transformation of Mammalian Cells", Molecular and Cellular Biology, Jun. 1987, vol. 7, pp. 2286-2293.

N.H. Patil & P.V. Devarajan, "Insulin-loaded alginic acid nanoparticles for sublingual delivery", Drug Delivery, (2016), 23(2), pp. 429-436, ISSN: 1071-7544. Also published online (Jun. 5, 2014) ISSN: 1521-0464, Journal homepage https://www.tandfonline.com/loi/idrd20.

Halwani, R. et al., "A novel anti-IL4Rα nanoparticle effieciently controls lung inflammation during asthma", Experimental & Molecular Medicine, (2016) vol. 48, 10 pgs.

Piktel, E. et al., "Recent insights in nanotechnology-based drugs and formulations designed for effective anti-cancer therapy", Journal of Nanobiotechnology, (2016) vol. 14, No. 39, 23 pgs.

Tang, J. et al., "Eudragit nanoparticles containing genistein: formulation, development, and bioavailability assessment", International Journal of Nanomedicine, (2011), vol. 6, pp. 2429-2435.

* cited by examiner

FORMULATIONS FOR ENTERIC DELIVERY OF THERAPEUTIC AGENTS

BACKGROUND

Proteins and peptides have been used for many years to treat diseases such as diabetes, heart disease, and cancer, and are used in vaccines. In most cases, the oral delivery of these agents fails due to the acidic conditions in the stomach. In addition, in vitro experiments have shown that many proteins and peptides are rapidly inactivated or destroyed in the presence of enzymes naturally occurring in the digestive tract. Finally, therapeutic proteins or peptides can be chemically or physically unstable in the presence of an excess of hydrogen ions or hydroxyl ions. Therefore, therapeutic proteins or peptides are generally delivered to patients parenterally.

Diabetes is characterized by chronic high blood glucose levels. As of 2014, an estimated 387 million people worldwide had diabetes, with especially high numbers in underdeveloped and developing countries. It is estimated that there will be 592 million diabetes patients by 2035. Therefore, diabetes is a critical global problem.

Insulin, a peptide hormone, is used to treat some forms of diabetes. It generally is delivered in liquid injection form because of its short half-life and degradation in the gastrointestinal tract. Because insulin must be administered frequently in an injectable form, patients, especially children, find it inconvenient. Therefore, there is great demand for the development of a more convenient non-injectable form of insulin, such as an oral dosage form.

While oral delivery of peptides, proteins, and other biologics is desirable, suitable formulations are challenging to design. Different coatings have been proposed to protect therapeutic proteins from degradation by stomach acid, including the use of pH-sensitive polymers. The pH of the human gastrointestinal tract increases progressively from the stomach (pH 2-3), to the small intestine (pH 6.5-7.0), to the colon (7.0-7.8). In the stomach, pH-sensitive polymers ideally resist the degrading action of gastric fluid, and the drug molecules are thus protected. After gastric emptying, the drug travels to the intestine, and the pH-sensitive polymer becomes soluble. Thus, the drug can be released in a controlled manner in the intestine by a combination of drug dissolution and diffusion through pores in the polymer matrix.

Various methods have been used to prepare pH-sensitive particles for oral delivery of protein or peptide therapeutics. The methods include lyophilization, spray drying, multiple emulsion-solvent evaporation, nanoprecipitation, and coacervation (Current Drug Therapy, 7:219-234, 2012). However, each of these methods has its drawbacks.

Solvent evaporation is a common method to prepare solid solutions or dispersions by dissolving drug and carrier in a solvent and then evaporating the solvent. The resultant solid mass is ground and sieved. However, it is difficult with this method to scale up and to achieve physical and chemical stability.

Co-precipitation of drug and polymer has been used as a means of increasing the dissolution of lipophilic drugs. Nanoprecipitates are prepared by transferring a solution of drug and polymer in a water-miscible solvent into an aqueous solution containing a stabilizer. Co-precipitates are formed instantaneously by rapid solvent diffusion.

In the emulsification-evaporation method, a solution containing drug and polymer in a water immiscible solvent (e.g., dichloromethane or chloroform) is emulsified into an aqueous solution containing an emulsifier. The subsequent evaporation of the solvent from the oil/water emulsion results in the formation of microparticles and/or nanoparticles. The emulsification-diffusion method is similar to the emulsification-evaporation method, but uses a partially water-soluble solvent (e.g., benzyl alcohol). A large amount of water is needed to induce the diffusion of the solvent from the oil/water emulsion to form particles.

In the salting-out process, an organic solution of polymer and drug is emulsified into an aqueous phase containing an electrolyte (e.g., $MgCl_2$) and a stabilizer (e.g., polyvinyl alcohol). Sufficient water is subsequently added to the emulsion to induce the diffusion of the organic solvent into the water, leading to polymer precipitation and formation of microparticles and/or nanoparticles. A complicated purification stage is necessary to eliminate the high amounts of emulsifying agent and electrolyte.

PCT application WO 2010/113177 discloses an oral insulin pH-sensitive delivery agent containing insulin and a methacrylic acid/methylmethacrylate copolymer (EUDRAGIT L100). The agent is prepared by a double emulsion technique using liquid paraffin, which is unstable.

U.S. published patent application US 2010/021549 describes a core-shell particle containing insulin and pH-sensitive polymers, such as hydroxypropyl methylcellulose phthalate (HPMCP) and hydroxypropyl methylcellulose acetate succinate (HPMCAS). The release of insulin from the particle is slow in an acidic medium but fast in a neutral medium. The particle is prepared by a fluidized bed spraying technique, resulting in particles having a diameter of about 2 mm.

Jelvehgari, et al. (AAPS PharmSciTech, Vol. 11, No. 3, September 2010, Development of pH-sensitive Insulin Nanoparticles using Eudragit L100-55 and Chitosan with Different Molecular Weights) describe the formation of insulin-containing nanoparticles using a methacrylic acid/methylmethacrylate copolymer (EUDRAGIT L100) and chitosan of varying molecular weights. Briefly, 0.4 mL of 10 mg/mL insulin was mixed with the 0.2% chitosan and then injected into 24 ml of 0.2% (w/v) Eudragit L100-55 solution in ethanol. During injection, the mixture was stirred at 500 RPM for the precipitation of drug and polymer, and the resulting opalescent dispersion was filtered through a 20 µm pore filter. The insulin loading efficacy was 18-30%. The particles ranged in size from about 135 nm to about 200 nm.

Particle size is a crucial factor to determine the absorption, distribution, and in vivo performance of polymer-based formulations for oral delivery. In general, nanoparticles have a higher cellular uptake efficiency than microparticles. Bakhru et al (Oral Delivery of Proteins by Biodegradable Nanoparticles, Adv Drug Deliv Rev 2013; 65:811) and Panyam, J. and Labhasetwar, V. (Biodegradable Nanoparticles for Drug and Gene Delivery to Cells and Tissue, Adv Drug Deliv Rev 2003; 55:329) reported that the cellular uptake of poly(lactide-coglycolide) (PLGA) nanoparticles with a particle size of 100 nm is 2.5-fold higher than 1 µm microparticles and six-fold higher than 10 µm microparticles in Caco-2 cells. A similar phenomenon has been observed in rats, in which the cellular uptake of PLGA nanoparticles was 15-fold and 250-fold higher than 1 µm and 10 µm microparticles, respectively. Nanoparticles with a particle size <100 nm are efficiently taken up in Peyer's patches, and then absorbed into the systemic circulation (Woitiski C B, et al. Strategies Toward the Improved Oral Delivery of Insulin Nanoparticles via Gastrointestinal Uptake and Translocation, BioDrugs 2008; 22:223).

There is a need for improved methods that are also cost-effective and easily scalable for industrial production of pH-sensitive particles for oral delivery. There is also a need for methods of preparing pH-sensitive particles that do not involve water-insoluble or toxic organic solvents, or that avoid the use of organic solvents altogether. Further, there remains a need for pH-sensitive particles for oral delivery of proteins, peptides, and other therapeutics with high loading efficiency and good bioavailability.

SUMMARY OF THE INVENTION

The present invention provides compositions containing nanoparticles for enteric delivery of therapy agents, and methods for making the nanoparticles.

One aspect of the invention is a composition for use in an oral formulation of a therapeutic agent. The composition includes a plurality of nanoparticles having a mean particle size of 50 nm or less, thereby offering high bioavailability. The composition includes a pH-sensitive polymer and a therapeutic agent having a molecular weight of about 10000 Daltons or less. In a preferred embodiment, the therapeutic agent has a molecular weight between about 1000 and about 10000 Daltons. In certain embodiments, the therapeutic agent is associated with, adhered to, or embedded within the nanoparticles. In certain embodiments, the nanoparticles consist essentially of the pH-sensitive polymer and the therapeutic agent. In some embodiments, the composition further includes a component selected from the group consisting of a surfactant, a lipid, a mucoadhesive polymer, and combinations thereof. In certain embodiments, the composition dissociates at a pH greater than about 5.0. In certain preferred embodiments, less than 5% of the therapeutic agent is released from the nanoparticles in 2 hours in an aqueous solution at a pH of less than about 2.0.

In some embodiments, the nanoparticles described above have a mean particle size from about 10 nm to about 30 nm. In some embodiments, the therapeutic agent is a peptide, protein, nucleic acid, small molecule drug, or a combination thereof. In certain preferred embodiments, the therapeutic agent is insulin. In some embodiments, the pH-sensitive polymer includes, or is composed of, anionic polymers containing carboxyl groups. In some embodiments, the pH-sensitive polymer is an anionic co-polymer of methylmethacrylic acid and methacrylic acid, such as poly(methacrylic acid-co-methyl methacrylate) 1:1, poly(methacylic acid-co-methyl methacrylate) 1:2. In some embodiments, the pH-sensitive polymer is an anionic polymer of hydroxypropyl methylcellulose, such as hydroxypropyl methylcellulose phthalate, or hydroxypropyl methylcellulose acetate succinate.

Another aspect of the invention is a composition for an oral formulation of a therapeutic agent including a plurality of nanoparticles having a mean particle size of 100 nm or less. The composition includes a pH-sensitive polymer and a therapeutic agent having a molecular weight of greater than about 10000 Daltons. In preferred embodiments, the therapeutic agent has a molecular weight from greater than about 10000 Daltons to about 400000 Daltons. In certain embodiments, the composition consists essentially of the pH-sensitive polymer and the therapeutic agent. In some embodiments, the composition further includes a component selected from the group consisting of a surfactant, a lipid, a mucoadhesive polymer, and combinations thereof. In preferred embodiments, the composition dissociates at a pH greater than about 5.0. In certain preferred embodiments, less than 5% of the therapeutic agent is released from the nanoparticles in 2 hours in an aqueous solution at a pH of less than about 2.0. In some embodiments, the therapeutic agent is a peptide, a protein, a nucleic acid, an antibody, a vector, a virus-like particle, a vaccine, or a combination thereof. In certain preferred embodiments, the therapeutic agent is an antibody. In some embodiments, the antibody is selected from the group consisting of anti-EGFR, anti-Her2, anti-RSV, anti-interleukin, and anti-TNF. In some embodiments, the antibody is selected from the group consisting of cetuximab, trastuzumab, palivizumab, tocilizumab, and adalimumab. In some embodiments, the pH-sensitive polymer is an anionic co-polymer of methylmethacrylic acid and methacrylic acid, such as poly(methacrylic acid-co-methyl methacrylate) 1:1, poly(methacylic acid-co-methyl methacrylate) 1:2. In some embodiments, the pH-sensitive polymer is an anionic polymer of hydroxypropyl methylcellulose, such as hydroxypropyl methylcellulose phthalate, or hydroxypropyl methylcellulose acetate succinate.

Yet another aspect of the invention is a method of preparing an orally administrable formulation of a therapeutic agent. The method includes the steps of: (a) providing an aqueous solution including the therapeutic agent and a pH-sensitive polymer, the solution having a pH of greater than about 5.5 and containing nanoparticles; and (b) lowering the pH of the solution to less than about 4.0, whereby the therapeutic agent and the polymer co-precipitate and the polymer entraps the therapeutic agent, and wherein the polymer is capable of dissociation at a pH greater than about 5.0, releasing the therapeutic agent. In certain embodiments, step (a) includes providing an aqueous solution including the therapeutic agent and pH-sensitive polymer at a pH below 5.0 and then raising the pH to above 5.5 by the addition of a buffer at pH 5.5-8 or a solution containing a surfactant, such as taurocholate or another bile acid, a lipid, a buffer, and optionally one or more stabilizers for maintaining the activity of the therapeutic agent. In some embodiments, the pH is raised to above 5.5 by the addition of a solution containing about 3 mM sodium taurocholate as the surfactant, about 0.75 mM phosphatidylcholine as the lipid, about 106 mM sodium chloride, and about 28 mM sodium phosphate adjusted with NaOH to pH 6.5. In some embodiments, the pH is raised to above 5.0 using a buffer such as acetate, succinate, citrate, histidine, phosphate, Tris, or the like, or using a base such as sodium hydroxide. In some embodiments, the pH is lowered in step (b) by the addition of HCl. In certain embodiments, the method further includes lyophilizing the formulation resulting from step (b).

In some embodiments of the method described above, the therapeutic agent has a molecular weight of less than about 10000 Daltons and the resulting formulation includes a plurality of nanoparticles having a mean particle size of about 50 nm or less. In some embodiments, the therapeutic agent has a molecular weight of more than about 10000 Daltons and the resulting formulation includes a plurality of nanoparticles having a mean particle size of about 100 nm or less. In some embodiments, the pH-sensitive polymer is an anionic co-polymer of methylmethacrylic acid and methacrylic acid, such as poly(methacrylic acid-co-methyl methacrylate) 1:1, poly(methacylic acid-co-methyl methacrylate) 1:2. In some embodiments, the pH-sensitive polymer is an anionic polymer of hydroxypropyl methylcellulose, such as hydroxypropyl methylcellulose phthalate, or hydroxypropyl methylcellulose acetate succinate. In some embodiments, the therapeutic agent is a peptide, protein, nucleic acid, small molecule drug, or a combination thereof. In preferred embodiments, an oral formulation of a therapeutic agent is prepared by the above described method.

Another aspect of the invention is method of treating a disease, or to aid in treating a disease. The method includes orally administering any of the compositions described above to a subject in need thereof. The composition includes a therapeutic agent that aids in treating the disease. In some embodiments, the therapeutic agent is insulin and the disease is diabetes, metabolic syndrome related to insulin deficiency, or diabetic ketoacidosis in an infant, child, or adolescent. In other embodiments, the therapeutic agent is an antitumor antibody and the disease is cancer. In certain embodiments, the therapeutic agent is an anti-inflammatory antibody and the disease is an inflammatory disease.

The invention also can be summarized with the following listing of embodiments.

1. An oral formulation of a therapeutic agent, the formulation comprising a plurality of nanoparticles having a mean particle size of 50 nm or less, the nanoparticles comprising a pH-sensitive polymer and a therapeutic agent having a molecular weight of about 10000 Daltons or less.
2. The formulation of embodiment 1, wherein the nanoparticles consist essentially of said pH-sensitive polymer and said therapeutic agent.
3. The formulation of embodiment 1, wherein the nanoparticles further comprise a component selected from the group consisting of a surfactant, a lipid, a mucoadhesive polymer, and a combination thereof.
4. The formulation of any of the preceding embodiments, wherein the nanoparticles dissociate at a pH greater than about 5.0, releasing the therapeutic agent.
5. The formulation of any of the preceding embodiments, wherein less than 5% of the therapeutic agent is released from the nanoparticles after 2 hours in an aqueous solution at a pH of less than about 2.0.
6. The formulation of any of the preceding embodiments, wherein the nanoparticles have a mean particle size from about 10 nm to about 30 nm.
7. The formulation of any of the preceding embodiments, wherein the therapeutic agent is a peptide, a protein, a nucleic acid, a small molecule drug, or a combination thereof.
8. The formulation of any of the preceding embodiments, wherein the therapeutic agent is insulin.
9. The formulation of any of the preceding embodiments, wherein the pH-sensitive polymer is hydroxypropyl methylcellulose acetate succinate or methylmethacrylate/methacrylate copolymer.
10. The formulation of any of the preceding embodiments, wherein the nanoparticles have a mean particle size of about 45 nm or less, or about 40 nm or less, or about 35 nm or less, or about 30 nm or less, or about 25 nm or less, or from about 5 nm to about 50 nm, or from about 5 nm to about 20 nm, or from about 5 nm to about 30 nm, or from about 5 nm to about 40 nm, or from about 10 nm to about 40 nm, or from about 20 nm to about 40 nm, or from about 20 nm to about 50 nm.
11. The formulation of any of the preceding embodiments, wherein the pH-sensitive polymer is substantially soluble in water at about 37° C. from pH of about 5.0 to pH about 8.0, or from about 4.5 to about 8.5, or from about 5.5 to about 8.0, or from about 6.0 to about 8.5, or from about 6.5 to about 8.5.
12. The formulation of any of the preceding embodiments, wherein the pH-sensitive polymer is substantially insoluble in water at about 37° C. from a pH of about 1.5 to pH about 3.5, or from about 1.0 to about 4.0, or from about 2.0 to about 4.0, or from about 1.0 to about 6.0, or from about 1.0 to about 6.5, or from about 1.0 to about 7.0, or from about 1.0 to about 7.5.
13. An oral formulation of a therapeutic agent, the formulation comprising a plurality of nanoparticles having a mean particle size of 100 nm or less, the nanoparticles comprising a pH-sensitive polymer and a therapeutic agent having a molecular weight of more than 10000 Daltons.
14. The formulation of embodiment 13, wherein the nanoparticles consist essentially of said pH-sensitive polymer and said therapeutic agent.
15. The formulation of embodiment 13 or embodiment 14, wherein the nanoparticles further comprise a component selected from the group consisting of a surfactant, a lipid, a mucoadhesive polymer, and a combination thereof.
16. The formulation of any of embodiments 13-15 wherein the nanoparticles dissociate or dissolve at a pH greater than about 5.0, releasing the therapeutic agent.
17. The formulation of any of embodiments 13-16, wherein less than 5% of the therapeutic agent is released from the nanoparticles after 2 hours in aqueous solution at a pH of less than about 2.0.
18. The formulation of any of embodiments 13-17, wherein the therapeutic agent is selected from the group consisting of a protein, a nucleic acid, an antibody, a vector, a virus-like particle, a vaccine, and a combination thereof.
19. The formulation of embodiment 18, wherein the therapeutic agent is an antibody selected from the group consisting of anti-EGFR, anti-Her2, anti-RSV, anti-interleukin, and anti-TNF, or selected from the group consisting of cetuximab, trastuzumab, palivizumab, tocilizumab, and adalimumab.
20. The formulation of any of embodiments 13-19, wherein the pH-sensitive polymer is hydroxypropyl methylcellulose acetate succinate or methylmethacrylate/methacrylate copolymer.
21. The formulation of any of embodiments 13-20, wherein the nanoparticles have a mean particle size of about 90 nm or less, or about 80 nm or less.
22. The formulation of any of embodiments 13-21, wherein the pH-sensitive polymer is substantially soluble in water at about 37° C. from pH of about 5.0 to pH about 8.0, or from about 4.5 to about 8.5, or from about 5.5 to about 8.0, or from about 6.0 to about 8.5, or from about 6.5 to about 8.5.
23. The formulation of any of embodiments 13-22, wherein the pH-sensitive polymer is substantially insoluble in water at about 37° C. from a pH of about 1.5 to pH about 3.5, or from about 1.0 to about 4.0, or from about 2.0 to about 4.0, or from about 1.0 to about 6.0, or from about 1.0 to about 6.5, or from about 1.0 to about 7.0, or from about 1.0 to about 7.5.
24. A method of preparing an orally administrable formulation of a therapeutic agent, the method comprising the steps of:
 (a) providing an aqueous medium comprising the therapeutic agent and nanoparticles comprising a pH-sensitive polymer, the medium having a pH of about 5.0 or higher; and
 (b) lowering the pH of the medium to less than about 4.0, whereby the polymer becomes tightly associated with the therapeutic agent.
25. The method of embodiment 24, wherein step (a) comprises providing an aqueous solution comprising the therapeutic agent and pH-sensitive polymer at a pH below 5.0 and then raising the pH to 5.0 or above by the addition of a solution containing a surfactant, a lipid, and a buffer.

26. The method of embodiment 25, wherein the pH is raised to above 5.0 by the addition of a solution containing a buffer at pH 5-8 and one or more stabilizing excipients, or a solution containing from 0 to about 10 mM sodium taurocholate as the surfactant, from 0 to about 1.5 mM phosphatidylcholine as the lipid, from 0 to about 150 mM sodium chloride, and from 0 to about 50 mM sodium phosphate as the buffer.

27. The method of any of embodiments 24-26, whereby the pH is lowered in step (b) by the addition of HCl.

28. The method of any of embodiments 24-27, further comprising:
(c) lyophilizing the formulation resulting from step (b).

29. The method of any of embodiments 24-28, wherein the therapeutic agent has a molecular weight of about 10000 Daltons or less and the resulting formulation comprises a plurality of nanoparticles having a mean particle size of about 50 nm or less, or wherein the therapeutic agent has a molecular weight more than about 10000 Daltons and the resulting formulation comprises a plurality of nanoparticles having a mean particle size of about 100 nm or less.

30. The method of any of embodiments 24-29, wherein the pH-sensitive polymer is hydroxypropyl methylcellulose acetate succinate or a methylmethacrylate/methacrylate copolymer.

31. The method of any of embodiments 24-30, wherein the therapeutic agent is selected from the group consisting of a peptide, a protein, a nucleic acid, an antibody, a vector, a vaccine, and a combination thereof.

32. An oral formulation of a therapeutic agent prepared by a method comprising the method of any of embodiments 24-31.

33. A method to aid in treating a disease, the method comprising orally administering the formulation of any of embodiments 1-23 to a subject in need thereof, wherein the formulation comprises a therapeutic agent that aids in treating said disease.

34. The method of embodiment 33, wherein the therapeutic agent is insulin and the disease is selected from the group consisting of diabetes, metabolic syndrome related to insulin deficiency, and diabetic ketoacidosis in an infant, child, or adolescent.

35. The method of embodiment 33, wherein the therapeutic agent is an antitumor antibody and the disease is cancer.

36. The method of embodiment 33, wherein the therapeutic agent is an anti-inflammatory antibody and the disease is an inflammatory disease.

DETAILED DESCRIPTION OF THE INVENTION

Figure 1:
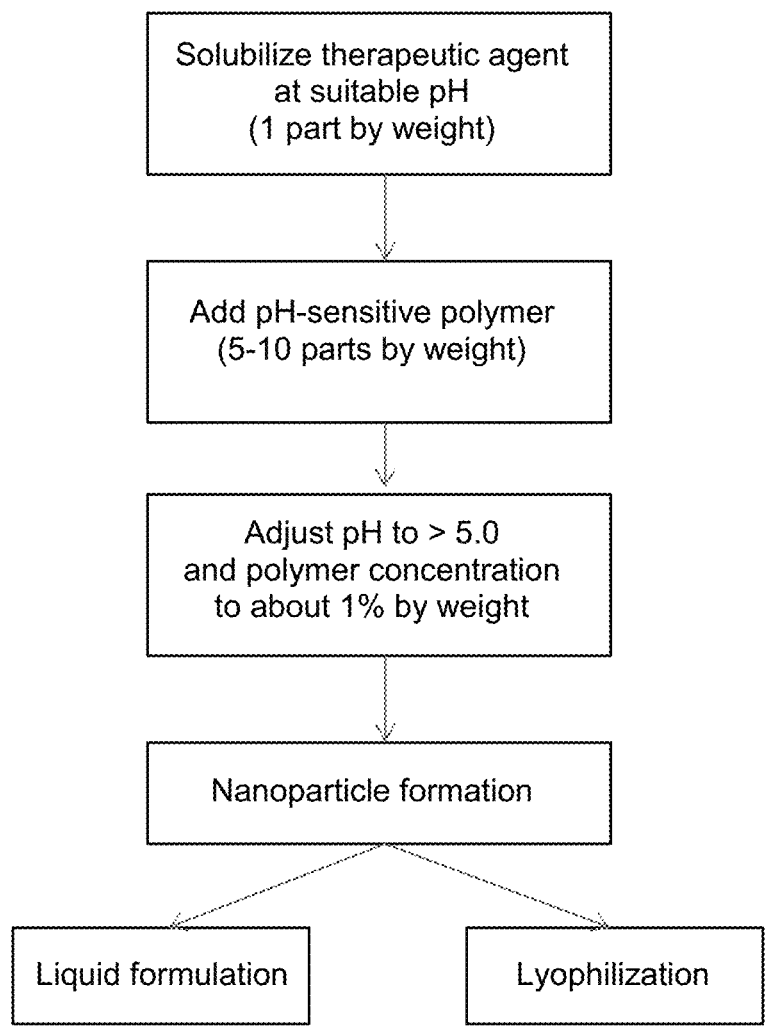
FIG. 1 is a flowchart of a solvent-free method for making nanoparticulate oral delivery formulations according to the invention.
Figure 2:
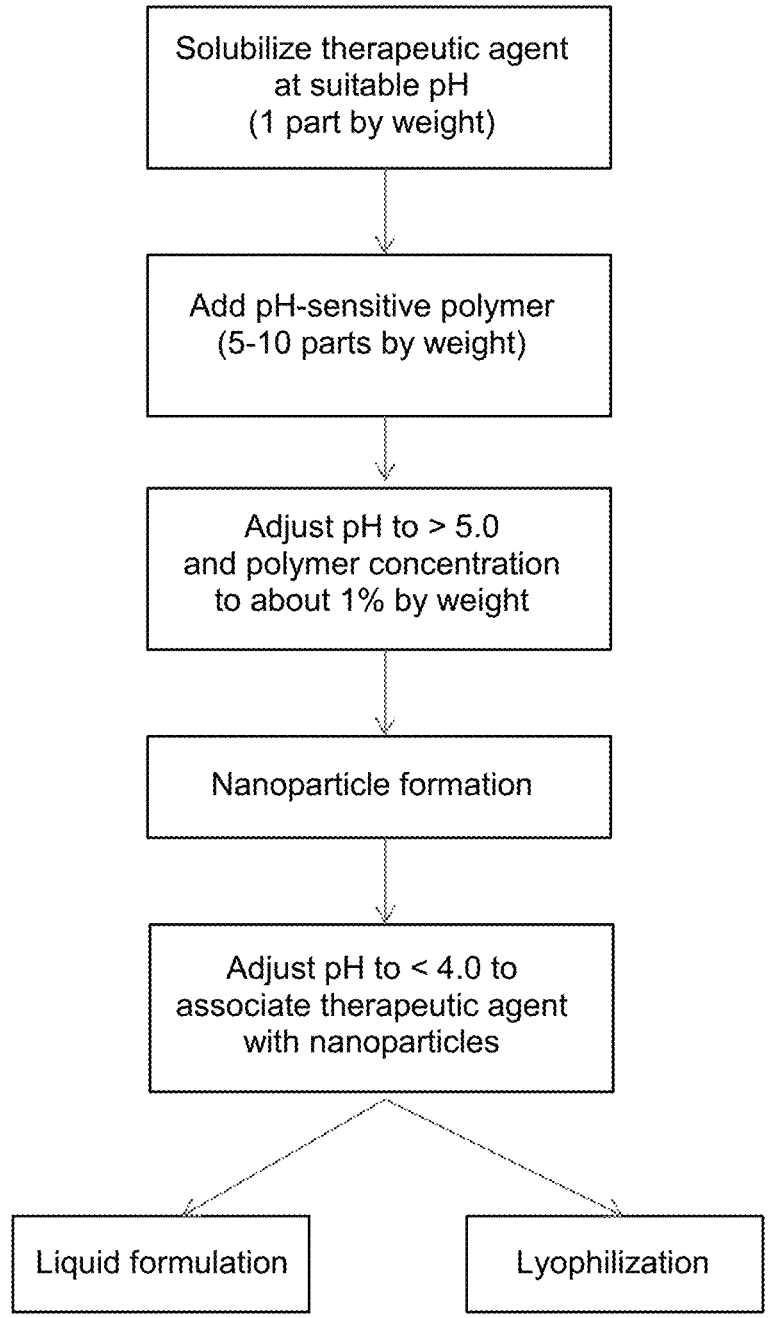
FIG. 2 is a flowchart of a modified solvent-free method for making nanoparticulate oral delivery formulations according to the invention.
Figure 3:
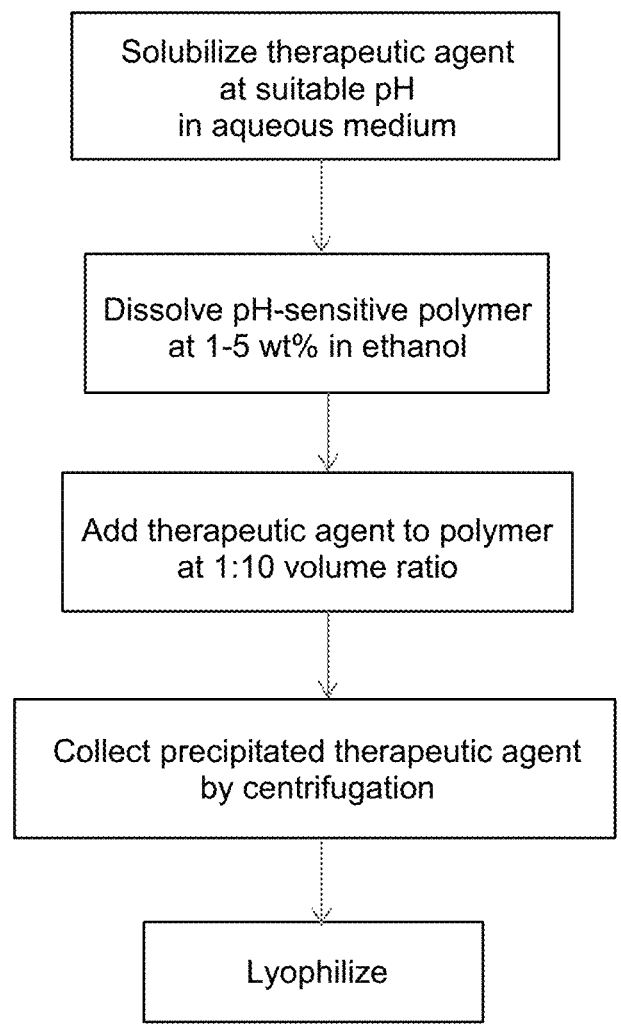
FIG. 3 is a flowchart of a solvent-based method for making nanoparticulate oral delivery formulations according to the invention.

The present invention provides pH-sensitive nanoparticle and microparticle compositions, methods of making the compositions, and methods for the oral delivery of therapeutic agents to treat diseases or medical conditions. The methods and formulations of the invention enable the protection of a wide variety of therapeutic agents in the gastric environment by forming a stable association of a therapeutic agent with a pH-sensitive polymer in the form of nanoparticles. The nanoparticles allow pH-dependent absorption of the therapeutic agent in the small intestine, leading to high bioavailability.

Without intending to limit the invention to any particular mechanism or molecular structure, it is believed that the nanoparticles of the invention provide a stable association between the polymer chains of the nanoparticles and the molecules of the therapeutic agent, wherein at low pH the therapeutic agent remains tightly associated with the polymer chains, thereby protecting the therapeutic agent from degradation at low pH. The pH-sensitive polymers used in the invention typically contain substituents that are neutral (protonated) at low pH but negatively charged (deprotonated) at neutral pH, leading to pH-dependent changes in particle size, such that the particles have nanoscale size at about neutral pH but microscale size at low pH. No external energy, such as sonication or heating, is necessary to generate the nanoparticles. The larger particle size at low pH (e.g., in the gastric environment) may enhance protection of the therapeutic agent, whereas the smaller particle size at neutral pH promotes absorption of the therapeutic agent. In some embodiments, the nanoparticles may entirely dissociate and their molecular components become completely solubilized at neutral pH. In other embodiments, the nanoparticles do not dissociate at neutral pH, but are of such small size as to allow good bioavailability by cellular absorption or paracellular transport.

An important property of the nanoparticle compositions of the invention is their very small size, which leads to higher bioavailability than obtained with previous particle compositions. The size of the nanoparticles at neutral pH is determined in part by the molecular size of the therapeutic agent. In general, the larger the molecular size of the therapeutic agent, the larger will be the size of the nanoparticles present at neutral pH. While in principle a continuum of nanoparticle sizes can be produced with methods of the invention, reflecting a continuum of molecular sizes of therapeutic agents, together with the pH dependence of the polymer, for convenience the nanoparticulate compositions are distinguished herein as being either "low molecular weight" or "high molecular weight" depending on the molecular weight of the therapeutic agent.

In low molecular weight embodiments of the invention, the nanoparticulate formulation includes a plurality of nanoparticles having a mean particle size of 50 nm or less, or about 45 nm or less, or about 40 nm or less, or about 35 nm or less, or about 30 nm or less, or about 25 nm or less. As used herein, "particle size" refers to the hydrodynamic diameter of a particle. Average hydrodynamic diameter can be determined, for example, using dynamic light scattering (DLS). Preferably, the nanoparticles of low molecular weight embodiments have a mean particle size of less than about 50 nm, or from about 10 nm to about 30 nm, or from about 15 nm to about 25 nm. In other embodiments, the nanoparticles have a mean particle size from about 5 nm to about 50 nm, or from about 5 nm to about 20 nm, or from about 5 nm to about 30 nm, or from about 5 nm to about 40 nm, or from about 10 nm to about 40 nm, or from about 20 nm to about 40 nm, or from about 20 nm to about 50 nm. The nanoparticles include a pH-sensitive polymer and a therapeutic agent having a molecular weight of about 10000 Daltons or less, or about 9000 Daltons or less, 8000 Daltons or less, 7000 Daltons or less, 6000 Daltons or less, 5000 Daltons or less, 4000 Daltons or less, 3000 Daltons or less, 2000 Daltons or less, or 1500 Daltons or less. In some embodiments, the therapeutic agent has a molecular weight from about 1000 to about 10000 Daltons, or from about 1000 Daltons to about 5000 Daltons, or from about 1000 Daltons to about 3000 Daltons, or from about 1000 Daltons to about 4000 Daltons, or from about 500 Daltons to about 5000 Daltons, or from about 3000 Daltons to about 5000 Daltons, or from about 5000 Daltons to about 10000 Daltons. In yet other embodiments, a low molecular weight form of the nanoparticle composition contains one or more therapeutic agents having a molecular weight from about 1000 Daltons to about 15000 Daltons, or from about 5000 Daltons to about 15000 Daltons, or from about 3000 Daltons to about 8000 Daltons.

In high molecular weight embodiments of the invention, the nanoparticulate formulation includes a plurality of nanoparticles having a mean particle size of about 100 nm or less, or about 90 nm or less, or about 80 nm or less, or about 110 nm or less, or about 120 nm or less, or about 130 nm or less, or about 140 nm or less, or about 150 nm or less, or about 30 nm to about 90 nm, or about 30 nm to about 100 nm, or about 40 nm to about 100 nm, or about 50 nm to about 100 nm, or about 60 nm to about 90 nm. The nanoparticles include a pH-sensitive polymer and a therapeutic agent having a molecular weight of about 10000 Daltons or more, for example, 15000 Daltons or more, 20000 Daltons or more, 25000 Daltons or more, 30000 Daltons or more, 40000 Daltons or more, or 50000 Daltons or more. In some embodiments, the therapeutic agent has a molecular weight of about 50000 Daltons or more, for example, 60000 Daltons or more, 70000 Daltons or more, 80000 Daltons or more, or 90000 Daltons or more. In other embodiments, the therapeutic agent has a molecular weight of more than about 10000 Daltons, such as about 11000 Daltons to about 20000 Daltons, or to about 30000 Daltons, to about 40000 Daltons, to about 50000 Daltons, to about 70000 Daltons, to about 100000 Daltons, to about 150000 Daltons, to about 200000 Daltons, to about 300000 Daltons, or to about 500000 Daltons.

The pH-dependent solubility of the nanoparticles of the invention is determined by the pH-dependent solubility of one or more polymers or co-polymers that are contained with the nanoparticles and form the matrix of the nanoparticles. A variety of pH-dependent polymers are known which are suitable for use in pharmaceutical compositions. Such polymers should be non-toxic, non-allergenic, available in pure form, and both physiologically and pharmacologically inert. Preferably they are also non-metabolizable. In certain preferred embodiments, the pH-sensitive polymer is an anionic polymer possessing a plurality of carboxyl groups distributed periodically along the length of the polymer backbone. In some embodiments, the pH-dependence of the aqueous solubility of the polymer, and also the size of nanoparticles or microparticles formed by the polymer, can be finely tuned by adjusting the amount or distribution of carboxyl or other substituent groups on the polymer chain. In certain embodiments, the pH-sensitive polymer is a copolymer of methacrylic acid and an acrylic or methacrylic ester. In certain embodiments, the pH-sensitive polymer is a methacrylic acid-methylmethacrylate copolymer, or a methacrylic acid-ethyl acrylate copolymer. In some embodiments, the pH-sensitive polymer is poly(methacrylic acid-co-methyl methacrylate) 1:1, poly(methacrylic acid-co-methyl methacrylate) 1:2, or a combination of both, and the ratio of carboxyl groups to ester groups (carboxyl/ester ratio) of poly(methacrylic acid-co-methyl methacrylate) can be manipulated to control the polymer pH sensitivity. In certain embodiments, the pH-sensitive polymer is preferably a methylmethacrylate-methacrylic acid copolymer, for example a methylmethacrylate-methacrylic acid copolymer having a molar ratio of about 1:1 of methylmethacrylate to methacrylic acid. In certain embodiments, the pH-sensitive polymer has a molecular weight from about 60,000 to about 200,000 Daltons. In some embodiments, the pH-sensitive polymer is a cellulose derivative, such as cellulose acetate phthalate (CAP), cellulose acetate succinate (CASE), cellulose acetate trimellitate (CAT), hydroxypropyl methylcellulose phthalate (or hypromellose phthalate) (HPMCP), or hydroxypropyl methylcellulose acetate succinate (or hypromellose acetate succinate) (HPMCAS), shellac gum, or polyvinyl acetate phthalate (PVAP). In certain embodiments, the pH-sensitive polymer is preferably hydroxypropyl methylcellulose acetate succinate, for example having a molecular weight from about 10,000 Daltons to about 500,000 Daltons. All of the above-mentioned polymers may be used individually or in combination to achieve the desired pH sensitivity, to control drug release or particle size, and to improve bioavailability of the drug upon oral administration.

A pH-dependent polymer for use in the invention is insoluble at acidic pH and soluble at neutral and/or alkaline pH. In some embodiments the pH-sensitive polymer is substantially soluble in water at about 37° C. from pH of about 5.0 to pH about 8.0, or from about 4.5 to about 8.5, or from about 5.5 to about 8.0, or from about 6.0 to about 8.5, or from about 6.5 to about 8.5. The pH-sensitive polymer is also substantially insoluble in water at about 37° C. from a pH of about 1.5 to pH about 3.5, or from about 1.0 to about 4.0, or from about 2.0 to about 4.0, or from about 1.0 to about 6.0, or from about 1.0 to about 6.5, or from about 1.0 to about 7.0, or from about 1.0 to about 7.5.

One useful measure of the solubility of the pH-sensitive polymer is the release of the therapeutic agent as a function of pH or other conditions. As used herein, "release" of a therapeutic agent refers to either the release of small nanoparticles containing associated therapeutic agent from microparticles containing associated therapeutic agent, or refers to the release of individual molecules of therapeutic agent from microparticles or nanoparticles, The release can be very rapid, such as within seconds or minutes, or it can be slow, taking hours or longer for a substantial amount of therapeutic agent to be released. An important parameter is the ability of the microparticles and/or nanoparticles to retain the therapeutic agent at acid pH. In certain embodiments, less than about 33% by mass of the therapeutic agent is released from the particles upon exposure of the particles to a solution of 0.01 N HCl at 23° C. for about 6 h. In other embodiments, more than 40% by mass of the therapeutic agent is released from the particles upon exposure of the particles to a solution of phosphate-buffered saline at pH about 6.8 at about 23° C. for about 1 h. Preferably, the microparticles/nanoparticles have both of these properties (i.e., very slow release at low pH and rapid and complete release at high pH. At high pH, the therapeutic agent should be released to a high degree (such as more than 30%, more than 40%, more than 50%, more than 60%, more than 70%, more than 80%, or more than 90%) within a physiologically or pharmacologically relevant timeframe (such as within 10 minutes, 30 minutes, 60 minutes, 90 minutes, or 120 minutes). At low pH, the therapeutic agent should not be substantially released during the time required for transit through the stomach. In certain embodiments, less than 5% of the therapeutic agent is released from the particles in 2 hours at a pH of less than about 2.0.

In certain embodiments, the mass ratio of therapeutic agent to pH-sensitive polymer is from about 10:1 to about 1:12, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, or about 1:12. In some embodiments, the mass ratio is from about 5:1 to about 1:5, or from about 3:1 to about 1:3, or from about 2:1 to about 1:2, or is about 1:1.

In some embodiments, the nanoparticles consist essentially of the pH-sensitive polymer and the therapeutic agent. In some embodiments, the nanoparticles and/or nanoparticle compositions and/or pharmaceutical compositions are essentially free of solvents. In other embodiments, the nanoparticles can further include one or more components such as buffers, surfactants, lipids, mucoadhesive polymers, stabilizing excipients, and combinations thereof. These additional components can be useful in maintaining solubility of the therapeutic agent during preparation of the nanoparticles or after release of the agent from the nanoparticles, or may be useful in preventing aggregation of the nanoparticles or promoting suspendability of the nanoparticles in aqueous solutions or water, and may also improve the bioavailability of the therapeutic agent. They may also improve the storability or useful half-life of the nanoparticles, and can help preserve the structure of the nanoparticles and/or bioavailability of the therapeutic agent after lyophilization. Mucoadhesive polymers can improve the adhesion of nanoparticles to the surface of the intestinal mucosa, leading to improved absorption into intestinal epithelial cells and eventually into the blood.

Surfactants can include anionic surfactants, including sodium oleate, sodium caprylate, sodium dodecyl sulfate, deoxycholate or sodium deoxycholate, taurocholate, or sodium taurocholate, dioctyl sodium sulfosuccinate, and sodium stearyl fumarate; nonionic surfactants, including polyoxyethylene ethers, polysorbate 80, and alkyl glycosides; and cationic surfactants, including quaternary ammonium compounds.

Lipids can include, for example, phospholipids (either neutral, cationic, or anionic), fatty acids (e.g., oleic acid, caprylic acid, linoleic acid, linolenic acid, sodium oleate, sodium linoleate, or sodium caprylate), fatty alcohols, and/or sterols. Lipids also include sphingolipids, including, but not limited to, sphingomyelin; glycosphingolipids including gangliosides, globocides and cerebrosides; and surfactant amines including, but not limited to, stearyl, oleyl and linoleyl amines.

As used herein, "phospholipid" is understood to be an amphiphilic derivative of glycerol, in which one of its hydroxyl groups is esterified with phosphoric acid and the other two hydroxyl groups are esterified with long-chain fatty acids that can be equal to or different from each other and can be saturated or unsaturated. A neutral phospholipid is generally one in which the other phosphoric acid hydroxyl is esterified by an alcohol substituted by a polar group (usually hydroxyl or amino) and whose net charge is zero. A phospholipid with a charge is generally one in which the other phosphoric acid hydroxyl is esterified by an alcohol substituted by a polar group and whose net charge is positive or negative.

Examples of phospholipids include phosphatidic acid ("PA"), phosphatidylcholine ("PC"), phosphatidylglycerol ("PG"), phophatidylethanolamine ("PE"), phophatidylinositol ("PI"), phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPF'), didecanoyl-L-alphaphosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), di stearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-olcoyl-phosphatidylinositol ("POPI"), diarachidoyl-phosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"). diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

As used herein, "fatty acid" means a compound whose structure is a carboxylic group attached to a hydrocarbon chain having one or more carbon atoms. The hydrocarbon chain may be saturated or unsaturated (i.e., alkyl, alkenyl or alkynyl hydrocarbon chains). Also, the hydrocarbon chain may be straight or branched. Moreover, in some embodiments, hydrogens in the hydrocarbon chain may be substituted.

As used herein, "fatty alcohol" means a compound whose structure is an alcohol group attached to a hydrocarbon chain having one or more carbon atoms. The hydrocarbon chain may be saturated or unsaturated (i.e., alkyl, alkenyl or alkynyl hydrocarbon chains). The hydrocarbon chain may be straight or branched. Moreover, in some embodiments, hydrogens in the hydrocarbon chain may be substituted.

As used herein, and unless otherwise specified, the term "fatty acid salt" means a compound formed from a reaction between a fatty acid and an inorganic/organic base. In addition, the term encompasses a compound formed from a reaction between a fatty alcohol and an inorganic/organic acid. Examples of such acids include sulfuric and phosphoric acid. The hydrocarbon chain of the fatty acid salt may be saturated or unsaturated (i.e., alkyl, alkenyl or alkynyl hydrocarbon chains). In addition, the hydrocarbon chain may be straight or branched. Moreover, in some embodiments, hydrogens in the hydrocarbon chain may be substituted.

Preferably the mass ratio of lipid to pH-sensitive polymer is from about 1:10 to about 8:1, for example, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, or about 8:1.

Mucoadhesive polymers can include, for example, hydroxypropyl methylcellulose, alginic acid, and polyxamer. Preferably a mucoadhesive polymer has a molecular weight from about 10,000 Daltons to about 150,000 Daltons, or from about 10,000 Daltons to about 300,000 Daltons, or from about 10,000 Daltons to about 600,000 Daltons.

In some embodiments, the low molecular weight therapeutic agent is a peptide, protein, nucleic acid, small molecule drug (i.e., any kind of pharmaceutical agent having a molecular weight of 1500 Daltons or less), or a combination thereof. Peptides can include antitumor peptides (e.g., leuprolide), peptides that treat metabolic diseases (e.g., insulin glargine, glucagon-like peptide-1 receptor agonists), peptide hormones (e.g., EPO), anti-infectious agents, (e.g., telavancin, protease inhibitors), analgesic/anesthetic peptides (e.g., enkephalin), and anti-inflammatory peptides. Proteins can include antitumor proteins (e.g., anti-VEGF agents, interferons, cytokines), proteins that treat metabolic diseases (e.g., insulin, glucagon), protein hormones (e.g., calcitonin, gonadotropin-releasing hormone), anti-infectious proteins (e.g., interferons), anti-inflammatory proteins (anti-TNF alpha agents), monoclonal antibodies, vaccines, enzymes, and enzyme inhibitors. Nucleic acids can include aptamers, small interfering RNAs, antisense oligonucleotides, and nucleic acids for gene editing and gene therapy, including viral vectors such as adenoviral vectors and lentiviral vectors. A preferred low molecular weight therapeutic agent is insulin.

The term "insulin", as used herein, refers to any naturally occurring or recombinant insulin. Accordingly, insulin for use in the invention includes, for example, insulin analogs and derivatives. Insulin from any suitable species can be used, such as human, pig, cow, dog, sheep. In a preferred embodiment, the insulin is recombinant human insulin. Naturally-occurring insulin or synthetic insulin can include monomeric, polymeric, and/or fibril-like insulin; it is understood that insulin molecules can take on different forms depending on pH.

In high molecular weight embodiments, the therapeutic agent can be, for example, a protein, a nucleic acid, an antibody, a virus-like particle, a vaccine, or a combination thereof. Proteins (whether high or low molecular weight, as defined herein) can include antitumor proteins (e.g., anti-VEGF agents, interferons, cytokines), proteins that treat metabolic diseases (e.g., insulin, glucagon), protein hormones (e.g., calcitonin, gonadotropin-releasing hormone), anti-infectious proteins (e.g., interferons), anti-inflammatory proteins (anti-TNF alpha agents), polyclonal antibodies, monoclonal antibodies, vaccines, enzymes, and enzyme inhibitors. Nucleic acids (whether high or low molecular weight as defined herein) include aptamers, small interfering RNAs, antisense oligonucleotides, gene editing and gene therapy.

Antibodies are preferred high molecular weight therapeutic agents for use in the invention. Such and antibody can be polyclonal, monoclonal, human, humanized, chimeric, or recombinant, and also can be an antigen-binding fragment of such an antibody. Monoclonal antibodies can be naturally occurring or recombinant immunoglobulin molecules. An antibody can be any class of immunoglobulin, such as IgG, IgM, IgA, IgD or IgE. Antibodies for use in the invention include antibody analogs and derivatives, such as antibody fragments (Fab, Fc, Fv), diabodies, triabodies, minibodies, nanobodies, single-domain antibodies such as scFv, and antibody fusion proteins. Preferred antibodies include antibodies that bind to EGFR, Her2, RSV, interleukin, and TNF, including cetuximab, trastuzumab, palivizumab, tocilizumab, and adalimumab, respectively.

In certain preferred embodiments, a composition of the invention is a pharmaceutical composition containing a plurality of any of the nanoparticles or microparticles of the invention, either in suspension in an aqueous medium or as a lyophilized material, together with one or more excipients, such as one or more carriers, fillers, binders, buffers, glidants, solutions, solvents, surfactants, electrolytes, salts, lubricants, disintegrants, swelling agents, antioxidants, or additional therapeutic agents not in nanoparticulate or microparticulate form. The pharmaceutical composition also can contain two or more different types of nanoparticles of the invention, having different therapeutic agents, or the same therapeutic agent in different nanoparticles having different release profiles. The pharmaceutical composition also can contain "blank" pH-dependent nanoparticles that carry no therapeutic agent. The pharmaceutical composition preferably is formulated for oral delivery, such as in the form of a capsule, tablet, or oral suspension in liquid. Specific embodiments of the pharmaceutical compositions are formulated for pediatric uses. In an embodiment, the formulation is a beverage or is suitable for reconstitution as a beverage, such as a fruit or vegetable juice, such as orange juice, or in a diary product such as milk or yogurt.

Fillers include lactose, saccharose, glucose, starch, microcrystalline cellulose, microfine cellulose, mannitol, sorbitol, calcium hydrogen phosphate, aluminum silicate, amorphous silica, sodium chloride, starch, and dibasic calcium phosphate dehydrate. In certain embodiments, the filler is not water soluble, although it may absorb water. In certain other embodiments, the filler is a spheronization aid. Spheronization aids can include one or more of crospovidone, carrageenan, chitosan, pectinic acid, glycerides, β-cyclodextrin, cellulose derivatives, microcrystalline cellulose, powdered cellulose, polyplasdone, crospovidone, and polyethylene oxide. In one embodiment, the filler includes microcrystalline cellulose.

Binders include cellulose ethers, methyl cellulose, ethyl cellulose, hydroxyethyl cellulose, propyl cellulose, hydroxypropyl cellulose, lower-substituted hydroxypropyl cellulose, hydroxypropyl methylcellulose (hypromellose, e.g., hypromellose 2910, METHOCEL E), carboxymethyl cellulose, starch, pregelatinized starch, acacia, tragacanth, gelatine, polyvinyl pyrrolidone (povidone), cross-linked polyvinyl pyrrolidone, sodium alginate, microcrystalline cellulose, and lower-substituted hydroxypropyl cellulose. In certain embodiments, the binders are selected from wet binders. In one type of embodiment, the binder is selected from cellulose ethers, e.g., hypromellose.

Disintegrants include starch, sodium cross-linked carboxymethyl cellulose, carmellose sodium, carmellose calcium, cross-linked polyvinyl pyrrolidone, sodium starch glycolate, low-substituted hydroxypropyl cellulose, and hydroxypropyl starch.

Glidants include polyethylene glycols of various molecular weights, magnesium stearate, calcium stearate, calcium silicate, fumed silicon dioxide, magnesium carbonate, magnesium lauryl sulfate, aluminum stearate, stearic acid, palmitic acid, cetanol, stearol, and talc.

Lubricants include stearic acid, magnesium stearate, calcium stearate, aluminum stearate, and siliconized talc.

A pharmaceutical composition also can include an aqueous medium, such as any water-based medium, e.g., water, saline solution, sugar solution, transfusion solution, or a buffer. An aqueous medium may contain one or more water-soluble organic solvents, such as ethanol, methanol, tetrahydrofuran, dimethylsulfoxide, etc., although in certain embodiments the pharmaceutical composition is solvent free. An aqueous medium is preferably sterile and suitable for use as a carrier of an active agent, and preferably has low concentrations of water-soluble organic solvents, if organic solvents are present at all. Examples of aqueous media include, but are not limited to, water for injection, saline solution, Ringer's solution, D5W, or other solutions of water-miscible substances such as dextrose and other electrolytes.

A pharmaceutical composition may contain a pharmaceutically acceptable salt, such as a salt prepared from pharmaceutically acceptable non-toxic acids or bases, including inorganic acids and bases, and organic acids and bases. Suitable pharmaceutically acceptable base addition salts for the compositions provided herein include metallic salts made from aluminum, calcium, lithium, magnesium, potassium, sodium, and zinc, or organic salts made from lysine, N,N'-dibenzylethylenediamine, chloroprocaine, choline, diethanolamine, ethylenediamine, meglumine (N-methylglucamine) and procaine. Suitable nontoxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Non-toxic acids include hydrochloric, hydrobromic, phosphoric, sulfuric, and methanesulfonic acids. Examples of specific salts thus include hydrochloride and mesylate salts.

The invention provides several methods for making oral formulations of therapeutic agents. One method is a solvent-free method that involves association of the therapeutic agent with a pH-sensitive polymer to form nanoparticles containing the agent and the polymer. An aqueous solution is provided that contains a soluble therapeutic agent and a pH-sensitive polymer. The solution initially has a pH of about 5.0-5.5, and subsequently the pH of the solution is lowered to less than about 4.0, whereby the therapeutic agent and the polymer associate. The polymer-therapeutic agent complex so formed remains stable at acidic pH. When the complex is orally administered to a mammalian subject, the therapeutic agent is not substantially degraded in the gastric environment, and is released in bioavailable form in the higher pH intestinal environment.

In an embodiment of this method, the therapeutic agent and the polymer are first added to an aqueous acidic solution (i.e., pH below about 5.5) and the pH is then raised to above about 5.5 by the addition of a solution containing a surfactant, a lipid, and a buffer such as acetate, succinate, citrate, histidine, phosphate, Tris, or the like, or a base such as sodium hydroxide. The polymer is insoluble at acidic pH and forms microparticles or nanoparticles (depending on the pH) associated with the therapeutic agent. The microparticles become small nanoparticles in the aqueous solution at a pH above 5.5, and in some embodiments the nanoparticles dissociate, releasing soluble therapeutic agent in molecular form or in a form not associated with particles of the polymer. In an embodiment, the pH is raised to above 5.5 by the addition of a solution containing about 3 mM sodium taurocholate, about 0.75 mM phosphatidylcholine, about 106 mM sodium chloride, and about 28 mM sodium phosphate adjusted with NaOH to about pH 6.5. In some embodiments, the pH is then lowered to less than about 4.0 by the addition of HCl. This method allows for the generation of very small nanoparticles with tightly associated therapeutic agent and high bioavailability upon oral administration. In embodiments, the therapeutic agent is insulin, and the nanoparticles formed have a small size below 50 nm, preferably below 30 nm, such as average size of about 18 nm, and the formation of the nanoparticles achieves about 100% association of the insulin with nanoparticles. Optionally, the formulation may then be lyophilized, stored, and later reconstituted in an aqueous medium for oral administration. The lyophilized nanoparticles can be formulated as a suspension, capsule, or tablet dosage form for oral administration. The lyophilized nanoparticles are released upon reconstitution as nanoparticles of the same or similar size compared to prior to lyophilization. The nanoparticles thus formed will not dissociate and the therapeutic agent will not be released in acidic pH, even if the agent is one that is highly soluble at acidic pH, such as insulin.

In another embodiment, referred to herein as the "modified solvent-free" method, the therapeutic agent and the polymer are added to a first aqueous medium suitable for formulating the therapeutic agent, and a second aqueous medium containing a buffer such as acetate, succinate, citrate, histidine, phosphate, Tris, or the like, or a base such as sodium hydroxide, and having a pH of about 6.5, is added to the first aqueous medium to raise the pH to above 5.0 and to form a third aqueous medium. The third aqueous medium is then lyophilized. Nanoparticles are formed prior to the lyophylization process, and are still present following reconstitution of the lyophilized material. The nanoparticles thus formed will not dissolve or dissociate and the therapeutic agent will not be released from particles at the acidic pH of the gastric environment, even if the agent is highly soluble at acidic pH. The lyophilized nanoparticles can be formulated as a suspension, capsule, or tablet dosage form for oral administration.

In preferred embodiments of the above described solvent-free methods, the concentration of the therapeutic agent in the aqueous medium is from about 0.05% to about 1.0% w/v, and more preferably from about 0.1% to about 0.3% w/v. In preferred embodiments of the above described solvent-free methods, the concentration of the polymer in the aqueous medium is from about 0.5% to about 10% w/v, and more preferably from about 1.0% to about 3.0% w/v.

Another aspect of the invention is a solvent-based method for preparing an orally administrable formulation of a therapeutic agent. The method includes adding one volume of an aqueous medium containing the therapeutic agent to about 2-10 volumes of an aqueous medium containing a pH-sensitive polymer dissolved in a water-miscible non-aqueous solvent, such as an organic solvent, whereby the therapeutic agent and pH-sensitive polymer form nanoparticles or microparticles containing the therapeutic agent. The suspension may then be centrifuged, and the precipitated nanoparticles or microparticles collected for storage or resuspension in another aqueous medium.

In preferred embodiments of the solvent-based method, the concentration of the therapeutic agent in the aqueous solution is from about 0.05% to about 1.0% w/v, and more preferably from about 0.1% to about 0.3% w/v. In preferred embodiments, the concentration of the polymer in the aqueous solution is from about 0.5% to about 10% w/v, and more preferably from about 1.0% to about 3.0% w/v.

In the solvent-based method, the water-miscible solvent can be any polar organic solvent, such as a linear, branched, or cyclic alcohol having between 1 and 6 carbon atoms, or it can contain at least one ketone, diketone, unsaturated ketone or cycloketone. In a preferred embodiment, the solvent is ethanol.

Another aspect of the invention is a method of treating a disease or medical condition, or to aid in treating a disease or medical condition. The method includes orally administering a composition, such as a pharmaceutical composition, containing a nanoparticle formulation according to the invention, to a subject in need thereof. The formulation comprises a therapeutic agent that aids in treating said disease. Preferably, the therapeutic agent is one that would be degraded or poorly absorbed if orally administered alone or using a conventional oral pharmaceutical formulation. The subject can be a mammal, such as a human.

In some embodiments, the therapeutic agent is insulin, and an insulin-containing composition of the invention is administered orally to treat diabetes, metabolic syndrome related to insulin deficiency, or diabetic ketoacidosis in an infant, child, or adolescent. The diabetes can be Type 1 or Type 2, and the subject can be any mammal or human in need of insulin administration. The oral administration of a composition of the invention can replace all or part of the conventional insulin therapy (e.g., insulin administered parenterally) of the subject.

In other embodiments, the therapeutic agent is an antitumor antibody (i.e., an antibody that leads to death of tumor cells by any mechanism), and it is administered to a subject to treat cancer in the subject. Antitumor antibodies include, but are not limited to anti-EGFR (e.g., cetuximab), anti-Her2 (e.g., trastuzumab), anti-RSV (e.g., palivizumab), anti-interleukin-(e.g., tocilizumab). The cancer can be any cancer susceptible to treatment with one or more antibodies, such as breast, colorectal, or head and neck cancer.

In yet other embodiments, the therapeutic agent is an anti-inflammatory antibody and the disease is an inflammatory disease. Anti-inflammatory antibodies include, but are not limited to, antibodies against tumor necrosis factor (TNF) and interleukin-6 (IL-6) receptor antagonists. Inflammatory diseases include, but are not limited to, Crohn's disease, rheumatoid arthritis, polyarticular juvenile idiopathic arthritis, and systemic juvenile idiopathic arthritis.

The nanoparticles or microparticles formed by this method can be employed in any dosage form, including pills, tablets, capsules, drinks, liquid suspensions or lyophilized powder. This composition can be employed by any route of administration, including oral, inhalational, buccal, sublingual, nasal, suppository or parenteral. Preferably, the formulation is for enteral administration, and even more preferably, oral administration.

The terms "formulation" and "composition" are used interchangeably herein.

EXAMPLES

Example 1

Materials and Methods

Fasted State Simulated Gastric Fluid (FaSSGF). Human FaSSGF was obtained from Biorelevant (London, UK). It contained 0.08 mM sodium taurocholate, 0.02 mM lecithin, 34.2 mM sodium chloride, and 25.1 mM hydrochloric acid. The pH of the solution was 1.6.

Fasted State Simulated Intestinal Fluid (FaSSIF). Human FaSSIF was obtained from Biorelevant (London, UK). It contained 3 mM sodium taurocholate, 0.75 mM lecithin, 105.9 mM sodium chloride, 28.4 mM monobasic sodium phosphate, and 8.7 mM sodium hydroxide. The pH of the solution was 6.5.

Solvent-Free Method. A therapy agent was dissolved and a pH-sensitive polymer was suspended in an acidic aqueous medium in which the therapeutic agent is soluble. Then, the pH was raised to 5.5 or higher by the addition of a solution containing 3 mM sodium taurocholate, 0.75 mM phosphatidylcholine, 106 mM sodium chloride, and 28 mM sodium phosphate, or the pH was raised to above 5.0 using a buffer such as acetate, succinate, citrate, histidine, phosphate, Tris, or the pH was adjusted with NaOH to 6.5. At pH 6.5, nanoparticles of the polymer were present. Subsequently, the pH was lowered to less than 4.0 with HCl so as to tightly associate the therapeutic agent with the particles. Optionally, this suspension was then lyophilized.

Modified Solvent-Free Method. A high molecular weight therapeutic agent and a pH-sensitive polymer were mixed in an aqueous medium, to which a solution at pH 6.5 was subsequently added, forming nanoparticles with associated therapeutic agent, and the suspension was then lyophilized. The lyophilized sample was then reconstituted with an appropriate aqueous solution or buffer.

Solvent-Based Method. A pH-sensitive polymer was solubilized in 100% ethanol to achieve a final concentration of about 1% to about 5% in solution. One volume of therapy agent in an aqueous solution was then added to 2-10 volumes of the organic solution containing the polymer. The solution was then centrifuged, and the precipitated nanoparticles were collected.

Modified Solvent-Based Method. A pH-sensitive polymer was solubilized in 100% ethanol to achieve a final concentration of about 1% to about 5% in solution. One volume of therapy agent in an aqueous solution at acidic pH (about pH 4.0 or less), where the agent was soluble, was taken and the pH was raised to about 5.0 or greater, resulting in precipitation of the therapeutic agent. Then, the so prepared therapeutic agent was added to 2-10 volumes of the organic solution containing the polymer, whereupon the polymer became associated with the precipitated therapeutic agent. The solution was then centrifuged, and nanoparticles containing the polymer and therapeutic agent were collected.

Insulin Enzyme-Linked Immunosorbent Assay (ELISA). Detection and quantification of insulin was conducted using Human Iso-Insulin Instant ELISA kits (Affymetrix/eBioscience Inc., San Diego, Calif., USA). Samples were diluted 100,000 fold before analysis and further diluted serially as recommended by the kit protocol.

Insulin High Performance Liquid Chromatography (HPLC). Detection and quantification of insulin was conducted by HPLC using an Agilent Zorbax C8 column. The solvent used was acetonitrile:water:trifluoroacetic acid and the eluted insulin peak was monitored as absorbance at 280 nm. The elution profile was as shown in Table 1 below.

TABLE 1

| Time in minute | Water % | Acetonitrile % | TFA % |
|---|---|---|---|
| 0 | 55 | 35 | 10 |
| 3.75 | 25 | 65 | 10 |
| 6.25 | 15 | 75 | 10 |
| 7.5 | 0 | 90 | 10 |
| 9.75 | 0 | 90 | 10 |
| 10.0 | 55 | 35 | 10 |
| 12.0 | 55 | 35 | 10 |

Lyophilization. For lyophilization, aliquots of solution were frozen at −50° C. for 2 hours and then heated to 20° C. with a ramp rate of 1° C., at a pressure of 75 mTorr. Lyophilization was carried out until the Pirani gauge in contact with the samples reached 75 mTorr or less.

Insulin Nanoparticle Formulations. Table 2 shows the composition of various nanoparticulate formulations that were made containing insulin as the therapeutic agent and EUDRAGIT L 100 as the pH-sensitive polymer. The formulations are discussed further in the examples below.

TABLE 2

Composition of Insulin Formulations (1 mL)

| Component | 1, 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|
| Sodium Taurocholate (mM) | 3 | 2.7 | 2.7 | 2.9 | 2.9 | 2.9 | 2.9 | 2.9 | 2.9 | 2.7 | 2.7 | 2.7 | 2.7 | 2.7 | 2.7 |
| Lecithin (mM) | 0.75 | 0.7 | 0.7 | 0.7 | 0.7 | 0.7 | 0.7 | 0.7 | 0.7 | 0.7 | 0.7 | 0.7 | 0.7 | 0.7 | 0.7 |
| Monosodium Phosphate (mM) | 28.36 | 25.5 | 25.5 | 27 | 27 | 27 | 27 | 27 | 27 | 25.2 | 25.1 | 25.1 | 25.1 | 25.1 | 25.1 |
| NaCL (mM) | 105.85 | 95.3 | 95.3 | 100.8 | 100.8 | 100.8 | 100.8 | 100.8 | 100.8 | 94.2 | 93.8 | 93.8 | 93.8 | 93.8 | 93.8 |
| NaOH (mM) | 8.7 | 7.8 | 7.8 | 8.3 | 8.3 | 8.3 | 8.3 | 8.3 | 8.3 | 7.7 | 6 | 6 | 6 | 6 | 6 |
| Final pH | 6.5 | 3.5 | 3.3 | 5.9 | 5.9 | 3.5 | 5.9 | 5.6 | 5.9 | 5.8 | 5.7 | 5.8 | 5.7 | 5.6 | 5.6 |
| EUDRAGIT L 100 (mg) | 10 | 10 | | 10 | 10 | 10 | 10 | 10 | 10 | 10 | 10 | 10 | 10 | 10 | 10 |
| Insulin (mg) | 1 | 2 | 2 | 2 | 2 | 2 | 2 | 2 | 2 | 2 | 2 | 2 | 2 | 2 | 2 |
| HPMC (mg) | | | 10 | 10 | | | | | | | | | | | |
| EUDRAGIT S-100 (mg) | | | 10 | | | | | | | | | | | | |
| Poloxamer (mg) | | | | | 10 | 10 | 10 | | | | | | | | |
| Alginate (%) | | | | | | | | 0.02 | | | | 0.01 | | | |
| Hydromellose (%) | | | | | | | | 0.02 | | | 0.01 | | | | |
| Caprylic acid (mM) | | | | | | | 16 | | | | | | | 16 | |
| Oleic acid (mM) | | | | | | | | | 16 | | | | | | 16 |
| Chitosan (%) | | | | | | | | | | | | | 0.02 | | |

Example 2

Solubility of Insulin Nanoparticles Following Lyophilization

The composition of insulin Formulation 1 is described in Table 2. The formulation was lyophilized, and 10 mg of the lyophilized powder (containing 1 mg insulin) was then reconstituted with 1 mL of the pH 6.5 buffer, forming nanoparticles. 100 µL of 1N HCl was then added to the solution, thereby precipitating particles containing polymer (EUDRAGIT L 100) and insulin. HPLC analysis of the supernatant after centrifugation did not show any insulin, even though insulin is highly soluble in HCl, demonstrating that the insulin had become tightly associated with the particles. Nevertheless, when the precipitate after centrifugation was solubilized in PBS at pH 7.2, the previously precipitated polymer became suspended, allowing for the complete recovery of insulin (1 mg) in solubilized or suspended form in PBS based on RP-HPLC analysis.

Example 3

Size Distribution and Solubility of Insulin Nanoparticles

Figure 4:
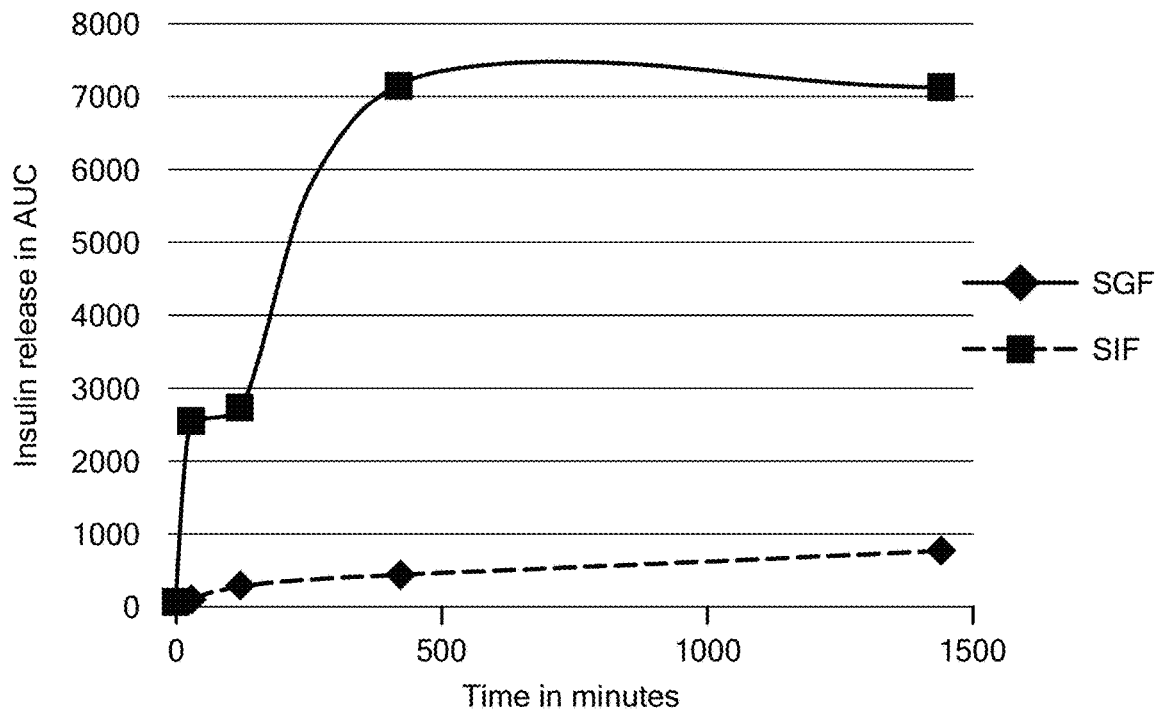
FIG. 4 shows the time course of insulin release from an insulin formulation produced by the solvent-free method. The release medium was simulated gastric fluid (SGF) or simulated intestinal fluid (SIF). Insulin concentration is expressed in units of area under the curve (AUC) for the insulin peaks obtained by HPLC fractionation of the medium.

Two 5-ml samples of Formulation 2 were adjusted to pH 2.5, which caused microparticle precipitation. The samples were then centrifuged at 3000 rpm to sediment the particles. The supernatant was analyzed with HPLC, which showed no insulin, indicating tight association of insulin with the precipitated particles. To the pellet of each sample, 5 mL of either FaSSIF or FaSSGF was added to resuspend the particles at pH 6.5 (FaSSIF) or pH less than 2.0 (FaSSGF). The insulin release profiles were monitored, and the data are shown in FIG. 4. The data indicate that insulin was released FaSSIF (pH 6.5) but hardly released in FaSSGF (acidic pH). The size of the resuspended particles was analyzed using a Zetasizer (Malvern Instruments, Malvern, UK) and the software provided by the manufacturer. The resuspended particles had a Z average diameter of 20.76 nm.

Example 4

HPLC Analysis of Insulin Nanoparticles at Acidic and Neutral pH

Formulation 3 was prepared following the solvent-free method using EUDRAGIT S-100 as polymer. When the pH of the solution was lowered to 3.5 the particles were not soluble. When the particles were transferred to PBS at pH 7.2, the precipitated particles became completely suspended or soluble, providing complete recovery of the insulin in PBS.

Example 5

Reconstitution of Lyophilized Formulation in Orange Juice

Formulation 4 was prepared following the solvent-free method. When the pH was lowered to 3.5, the particles were not soluble, even though insulin is highly soluble in acidic pH. The particles were precipitated by centrifugation, and the precipitate was then solubilized in PBS at pH 7.2, with complete recovery of the insulin content based on RP-HPLC analysis. The precipitate was also reconstituted in ordinary, commercially available orange juice, and analysis of the orange juice showed that there was no free insulin in the liquid. However, when the pH was adjusted to 6.0, insulin-containing particles remained in the supernatant. This result suggests that the formulation, as reconstituted in orange juice or another fruit juice or acid drink, may be used as a pediatric formulation for diabetic patients.

Example 6

Insulin Nanoparticle Formulations Containing Mucoadhesive Polymers

Formulation 5 was prepared following the solvent-free method. The formulation was then divided into 1.2 mL aliquots in 3-mL flint glass vials and lyophilized. HPLC analysis showed that the reconstituted lyophilized powder release Insulin completely, as the polymer entrapped with the insulin is soluble at pH 5.9.

Formulation 6, containing the mucoadhesive polymer poloxamer, was prepared following the modified solvent-free method. The pH was adjusted to 3.5. The formulation was then divided into 1.2 mL aliquots in 3-mL flint glass vials and lyophilized. HPLC analysis showed that the reconstituted lyophilized powder does not release Insulin, as the polymer entrapped with the insulin is not soluble at pH 3.5.

Formulation 7, containing the mucoadhesive polymer poloxamer, was prepared following the solvent-free method. The formulation was then divided into 1.2 mL aliquots in 3-mL flint glass vials and lyophilized. HPLC analysis showed that the reconstituted lyophilized powder release Insulin completely, as the polymer entrapped with the insulin is soluble at pH 5.9.

Formulation 8, containing the mucoadhesive polymers alginate, hypromellose, and poloxamer, was prepared following the modified solvent-free nanoparticle formation method. The formulation was then divided into 1.2 mL aliquots in 3-mL flint glass vials and lyophilized. The final pH was 5.9. HPLC analysis showed that the reconstituted lyophilized powder release Insulin completely, as the polymer entrapped with the insulin is soluble at pH 5.9.

Example 7

Size of Nanoparticles Containing Fatty Acid Permeability Enhancers

Formulation 9, containing caprylic acid as permeability enhancer, was prepared by adding insulin and EUDRAGIT to an aqueous acidic solution, followed by the addition of NaOH, and then of the pH 6.5 buffer. To this solution, the permeability enhancer caprylic acid was added, and the pH of the formulation was adjusted to 5.6. The mean particle size of the formulation was 23 nm. One mL aliquots of the formulation were distributed in 20 mL vials and lyophilized. HPLC analysis showed that the reconstituted lyophilized powder release Insulin completely, as the polymer entrapped with the insulin is soluble at pH 5.6.

Formulation 10, containing oleic acid as permeability enhancer, was prepared by adding insulin and Eudragit to an aqueous acidic solution, followed by the addition of NaOH, and then of the pH 6.5 buffer. To this solution, the permeability enhancer oleic acid was added, and the pH of the formulation reached 5.6. The particle size of the formulation was 18.6 nm. One mL aliquots of the formulation were distributed in 20 mL vials and lyophilized. HPLC analysis showed that the reconstituted lyophilized powder release Insulin completely, as the polymer entrapped with the insulin is soluble at pH 5.9.

Example 8

Figure 5:
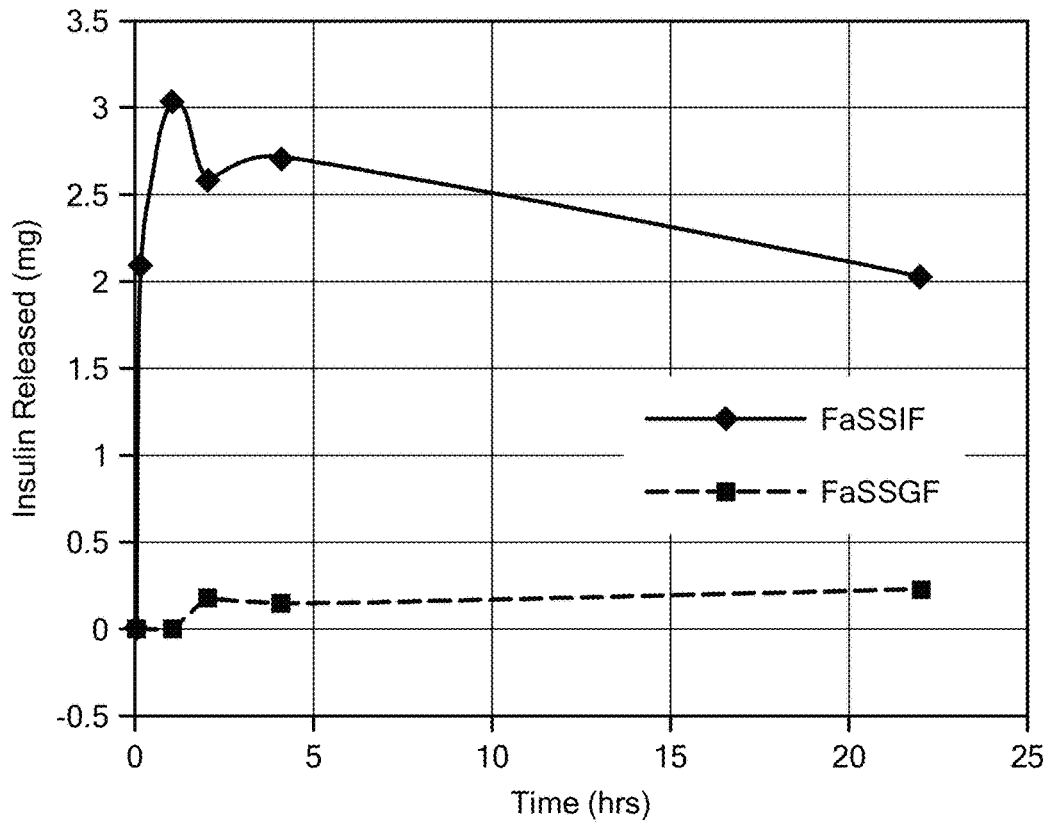
FIG. 5 shows the time course of insulin release from an insulin formulation in fasted state simulated gastric fluid (FaSSGF) and fasted state simulated intestinal fluid (FaSSIF). The amount of insulin released was measured using an insulin-specific ELISA.

Insulin Release from Lyophilzed Nanoparticle Formulations Reconstituted with FaSSIF or FaSSGF Formulation 11 had a mean particle size of 18.28 nm as measured by DLS. 1 ml samples were distributed in two 20 mL vials and lyophilized. One vial was reconstituted with FaSSGF, and the pH was adjusted to less than 2.0. The second vial was reconstituted with FaSSIF at pH 6.5. The insulin release profile was monitored using an insulin-specific ELISA for 24 hours. At each time point, the samples were centrifuged at 10,000 rpm for 5 minutes and the supernatant was assayed for its insulin content by ELISA. The release profile, shown in FIG. 5, indicated that insulin was released into the supernatant only at pH 6.5 and not at the acidic pH of less than 2.0.

Figure 6:
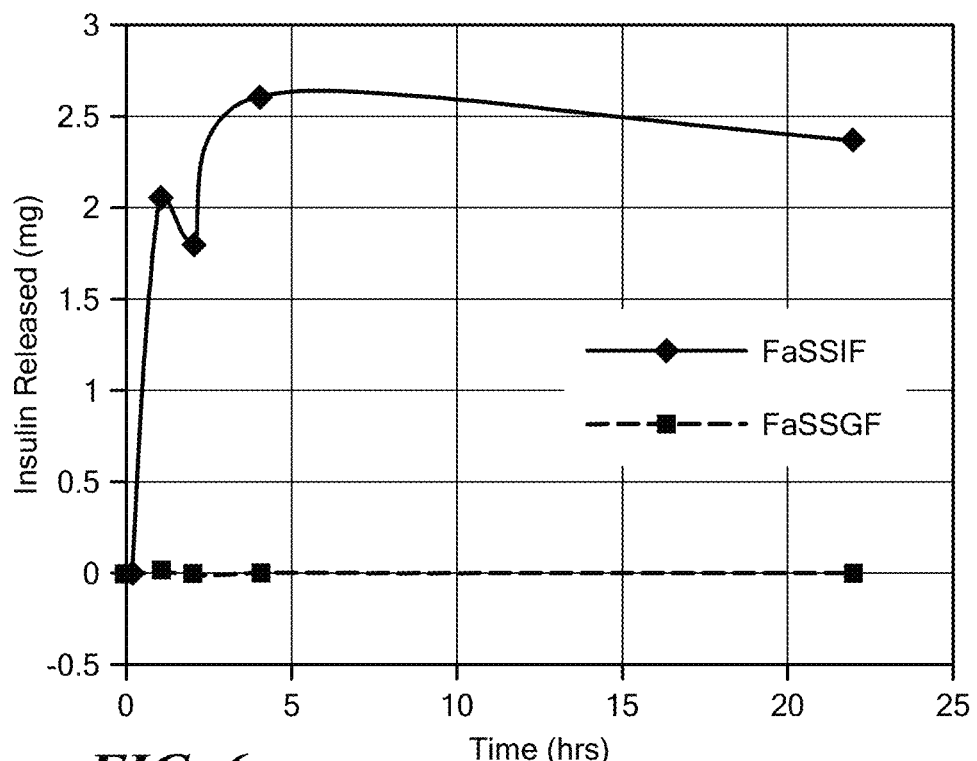
FIG. 6 shows the time course of insulin release from an insulin formulation in FaSSGF and FaSSIF using ELISA.
Figure 7:
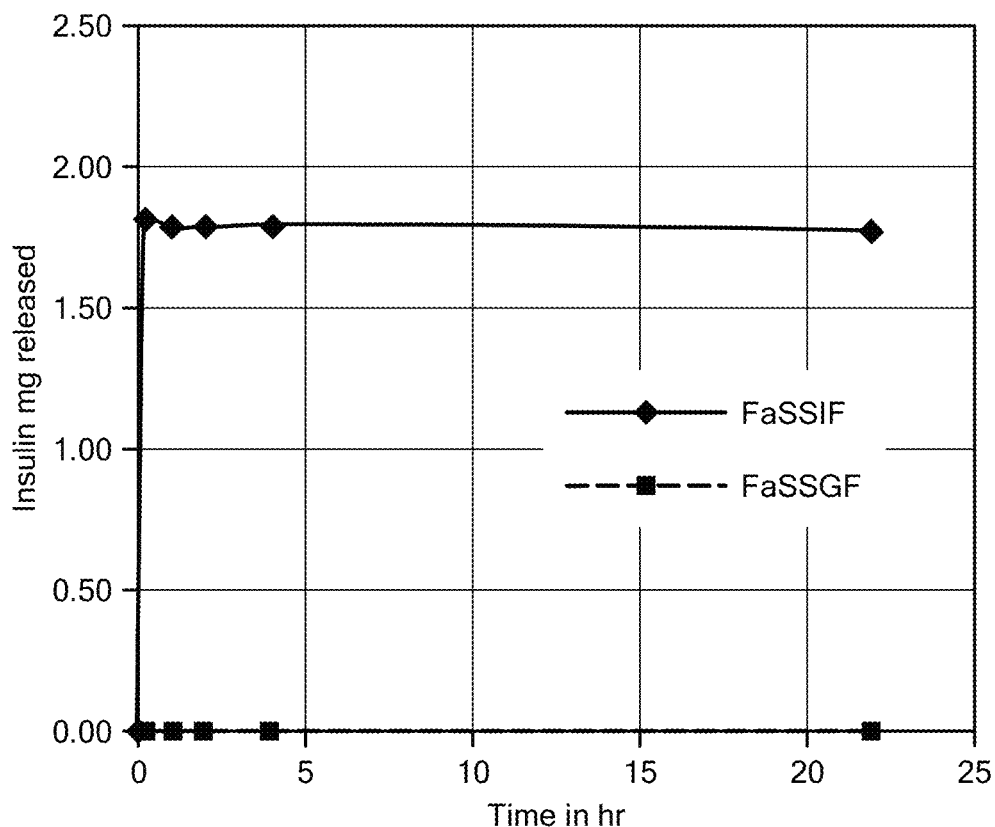
FIG. 7 shows the time course of insulin release from an insulin formulation in FaSSGF and FaSSIF using HPLC.

Formulation 12, containing the mucoadhesive polymer HPMC, had a mean particle size of 23.11 nm as measured by DLS. 1 ml aliquots were distributed in two 20 mL vials and lyophilized. One vial was reconstituted with FaSSGF, and the pH was adjusted to less than 2.0. The second vial was reconstituted with FaSSIF at pH 6.5. The insulin release profile was monitored for 24 hours. At each time point, the samples were centrifuged at 10,000 rpm for 5 minutes and the supernatant was assayed for its insulin content using both HPLC and ELISA. FIGS. 6 and 7 show the release profile determined by the two different methods. Both HPLC and ELISA indicated that insulin was released into the supernatant only at pH 6.5, and not at the acidic pH of less than 2.0, with the inclusion in the nanoparticles of the mucoadhesive polymer.

Figure 8:
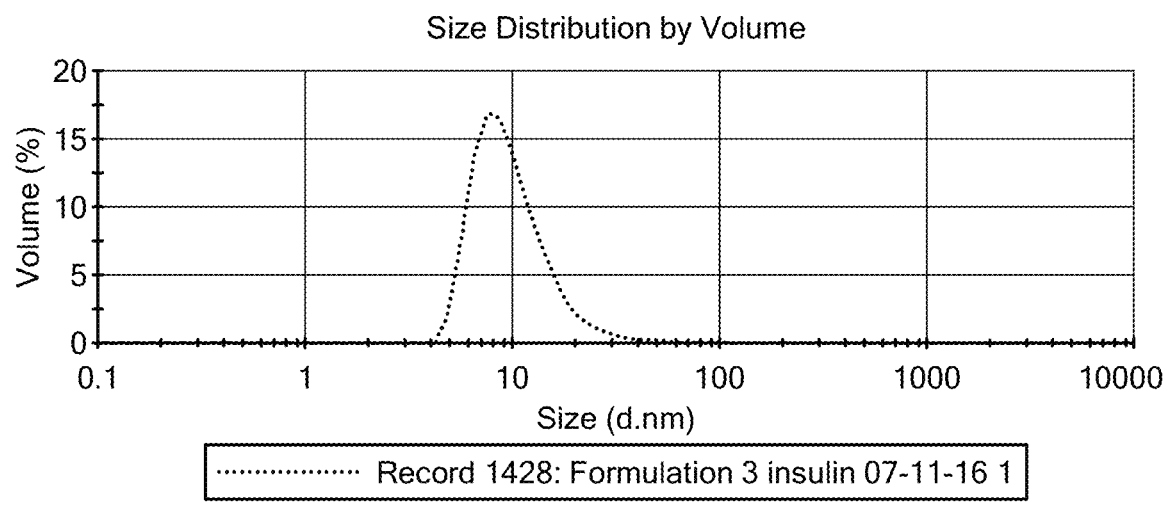
FIG. 8 shows particle size measurement using dynamic laser light scattering (DLS).
Figure 9:
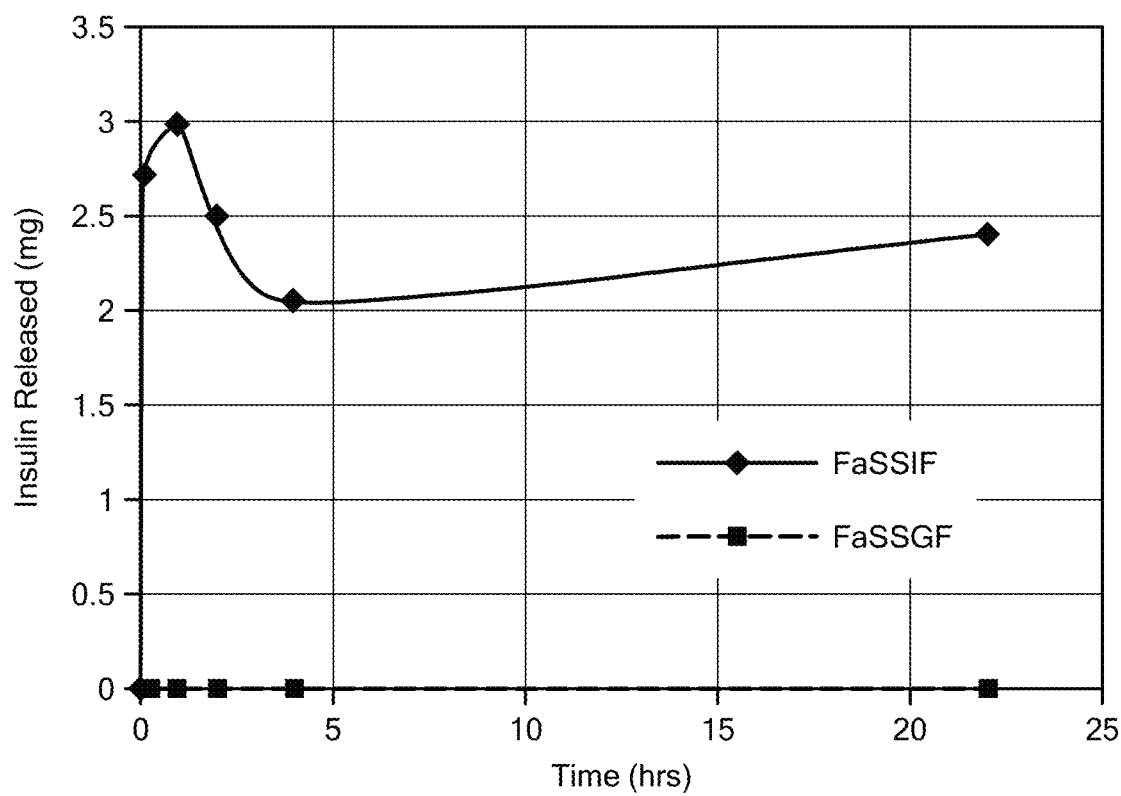
FIG. 9 shows the time course of insulin release from an insulin formulation in FaSSGF and FaSSIF using ELISA.

Formulation 13, containing the mucoadhesive polymer alginate, had a mean particle size of 18.79 nm as measured by DLS (FIG. 8). 1 ml aliquots were distributed in two 20 mL vials and lyophilized. One vial was reconstituted with FaSSGF, and the pH was adjusted to less than 2.0. The second vial was reconstituted with FaSSIF at pH 6.5. The insulin release profile was monitored for 24 hours by ELISA. At each time point, the samples were centrifuged at 10,000 rpm for 5 minutes and the supernatant was assayed for its insulin content. FIG. 9 shows the release profile. Insulin was released into the supernatant only at pH 6.5, and not at the acidic pH of less than 2.0, with the inclusion of alginate in the nanoparticles.

Figure 10:
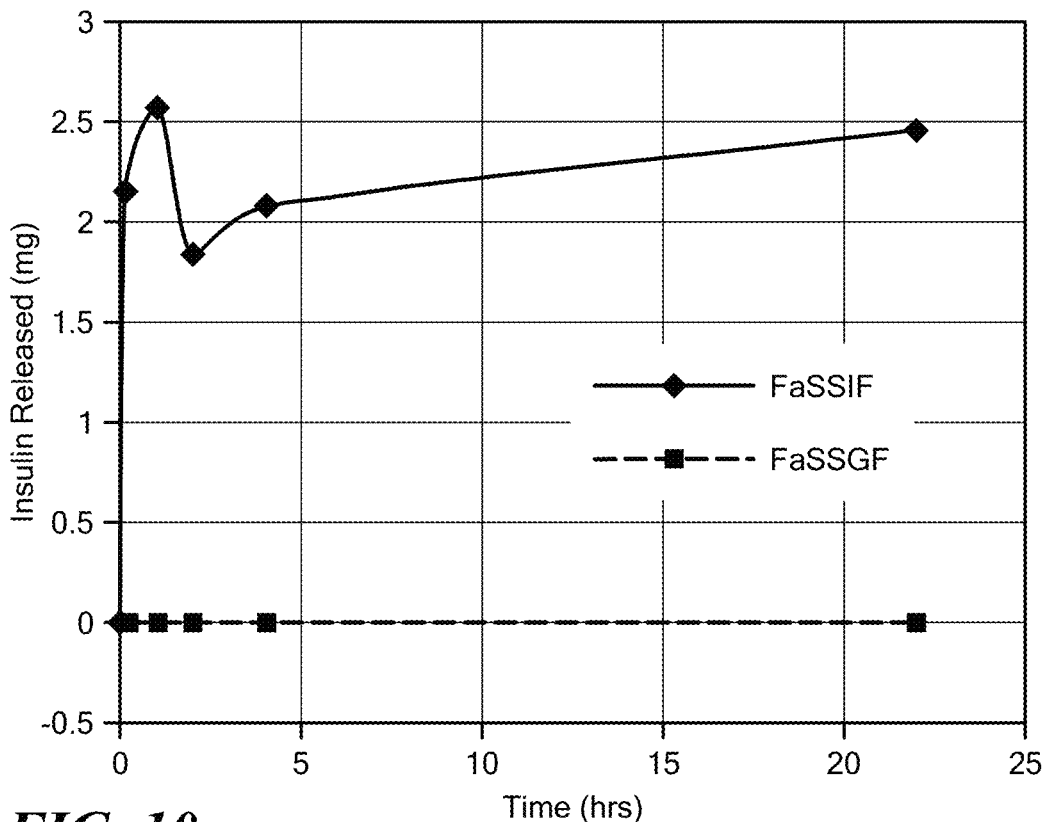
FIG. 10 shows the time course of insulin release from an insulin formulation in FaSSGF and FaSSIF using ELISA.
Figure 11:
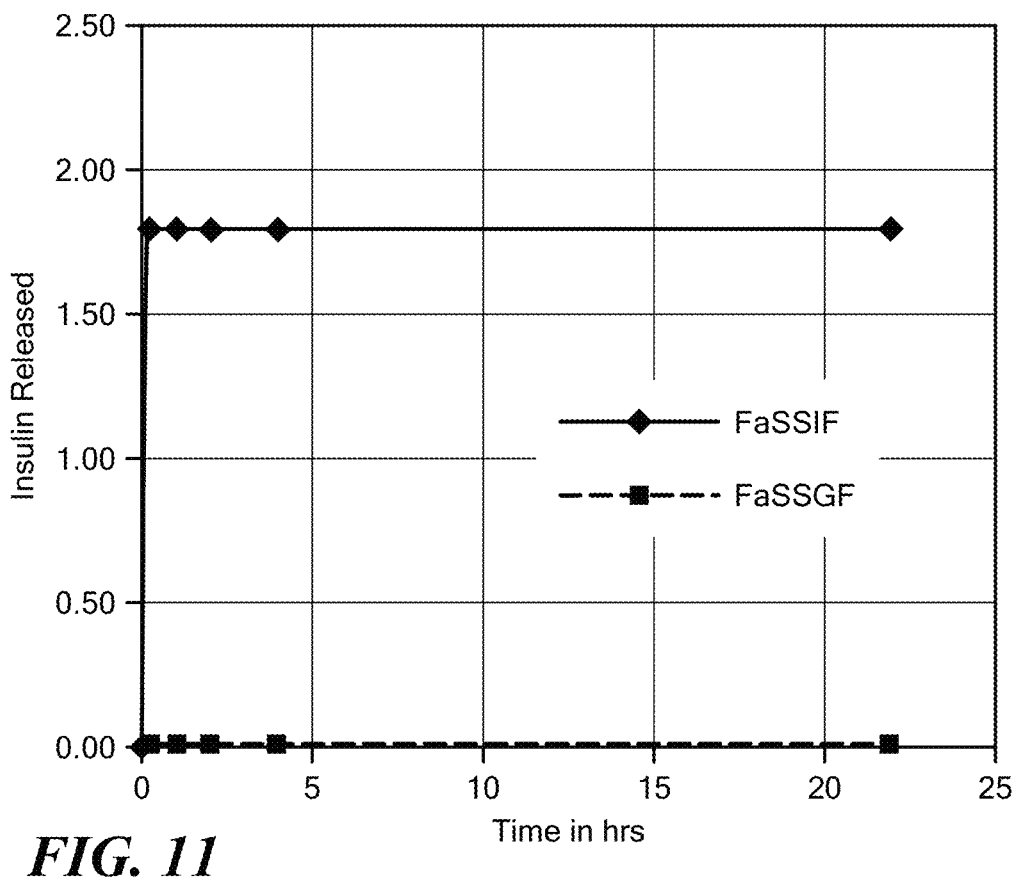
FIG. 11 shows the time course of insulin release from an insulin formulation in FaSSGF and FaSSIF using HPLC.

Formulation 14, containing the mucoadhesive polymer chitosan, had a mean particle size of 1577 nm as measured by DLS. The large particle size may have been due to insolubility of chitosan at pH 6.5. 1 ml aliquots were distributed in two 20 mL vials and lyophilized. One vial was reconstituted with FaSSGF, and the pH was adjusted to less than 2.0. The second vial was reconstituted with FaSSIF at pH 6.5. The insulin release profile was monitored for 24 hours. At each time point, the samples were centrifuged at 10,000 rpm for 5 minutes and the supernatant was assayed for its insulin content by both ELISA and HPLC. FIGS. 10 and 11 show the release profile for both methods. Insulin was released into the supernatant only at pH 6.5, and was not released at the acidic pH of less than 2.0, with the inclusion of chitosan in the nanoparticles.

Figure 12:
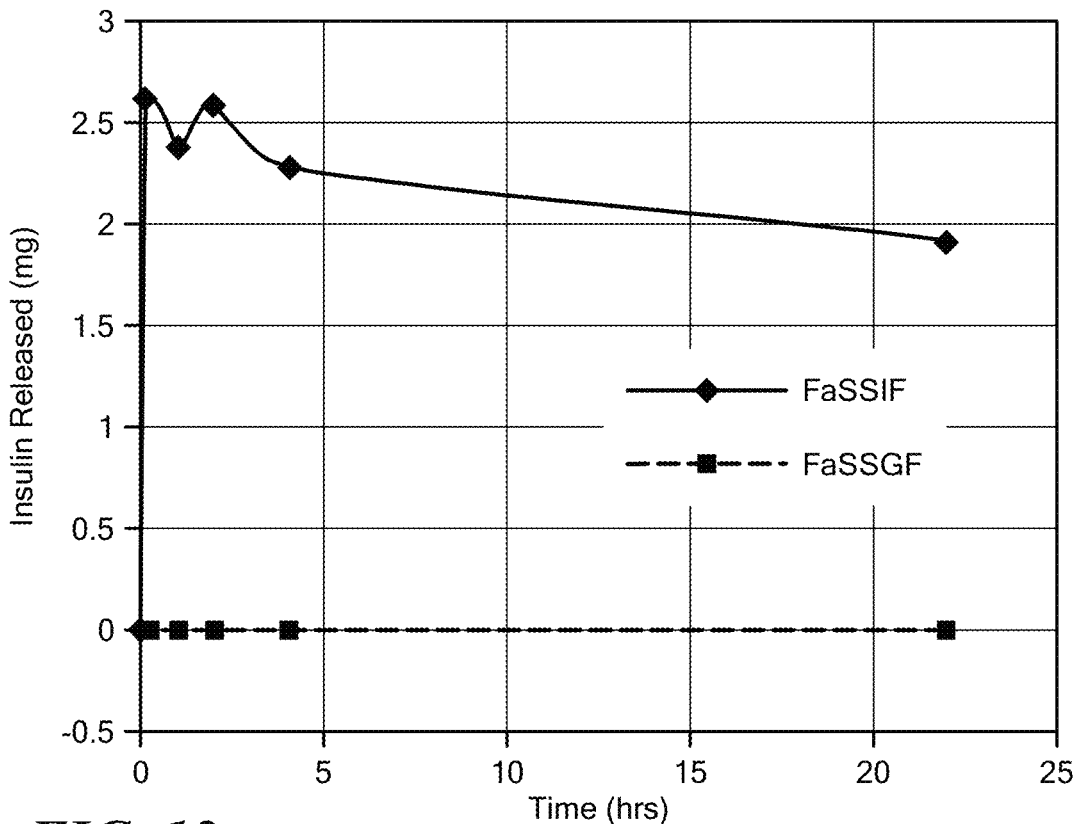
FIG. 12 shows the time course of insulin release from an insulin formulation in FaSSGF and FaSSIF using ELISA.
Figure 13:
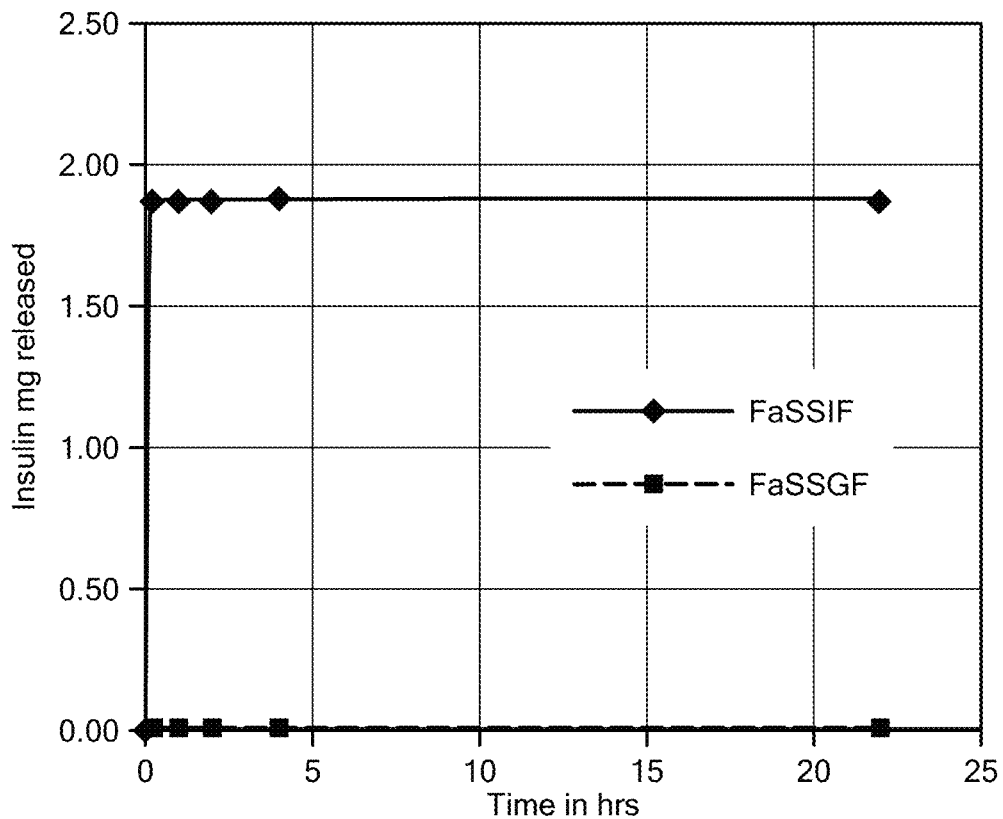
FIG. 13 shows the time course of insulin release from an insulin formulation in FaSSGF and FaSSIF using HPLC.

Formulation 15, containing caprylic acid as permeability enhancer, had a mean particle size of 23.67 nm as measured by DLS. One ml aliquots were distributed in two 20 mL vials and lyophilized. One vial was reconstituted with FaSSGF, and the pH was adjusted to less than 2.0. The second vial was reconstituted with FaSSIF at pH 6.5. The insulin release profile was monitored for 24 hours. At each time point, the samples were centrifuged at 10,000 rpm for 5 minutes and the supernatant was assayed for its insulin content by ELISA and HPLC. FIGS. 12 and 13 show the release profile. Insulin was released into the supernatant only at pH 6.5 and not at the acidic pH of less than 2.0 with the inclusion in the nanoparticles of caprylic acid.

Figure 14:
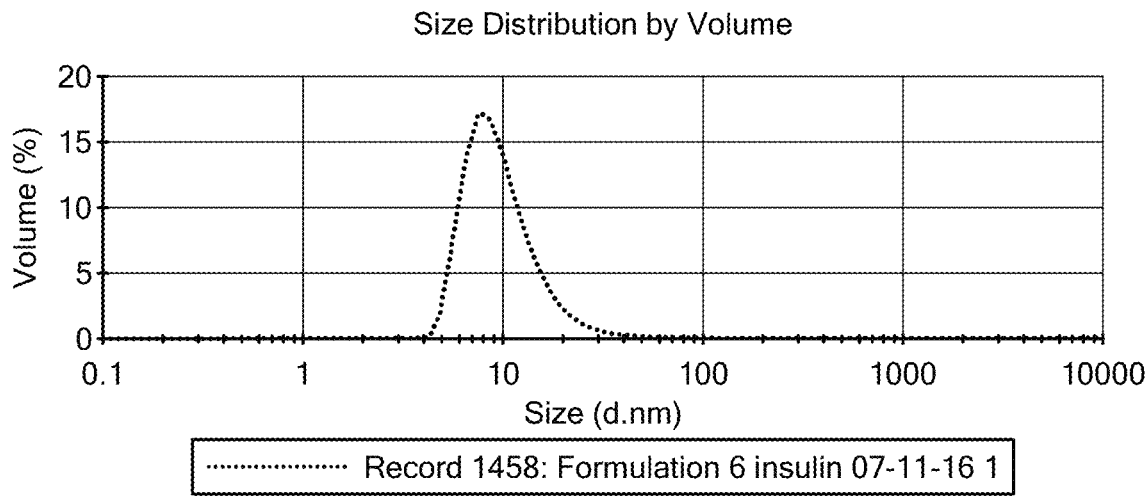
FIG. 14 shows particle size measurement using DLS.
Figure 15:
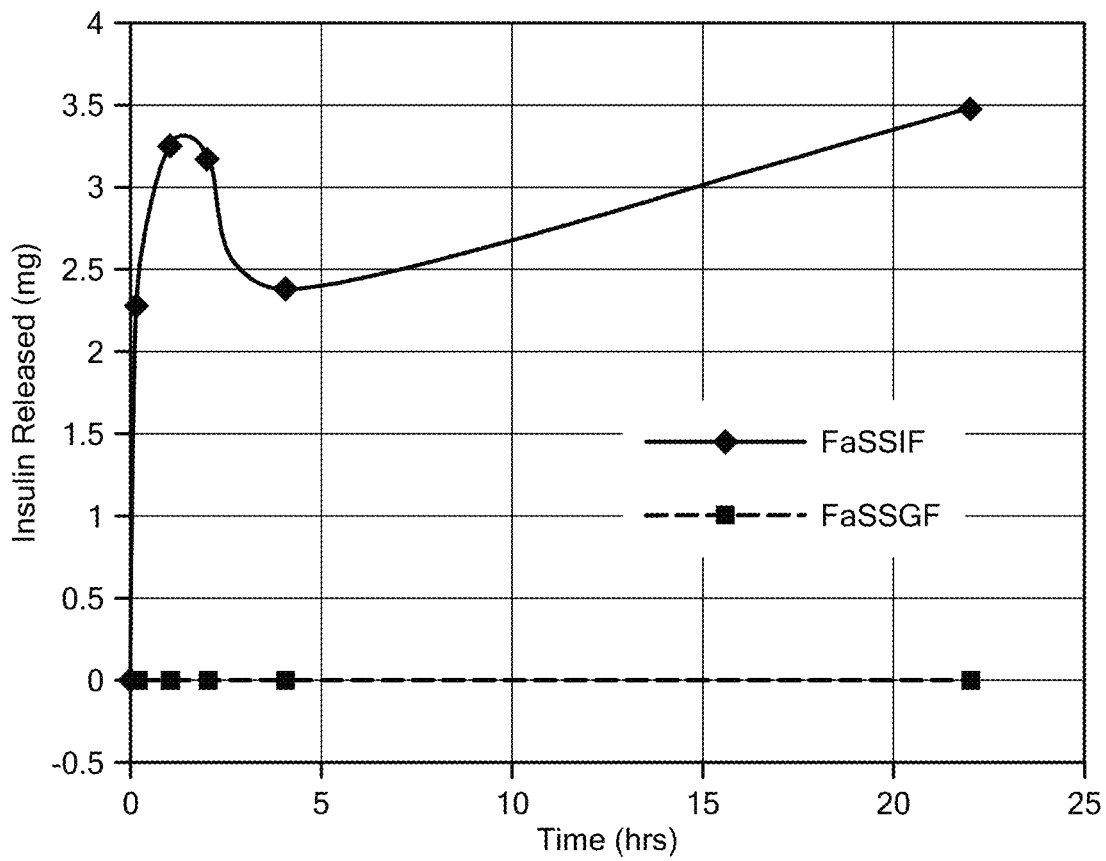
FIG. 15 shows the time course of insulin release from an insulin formulation in FaSSGF and FaSSIF using ELISA.
Figure 16:
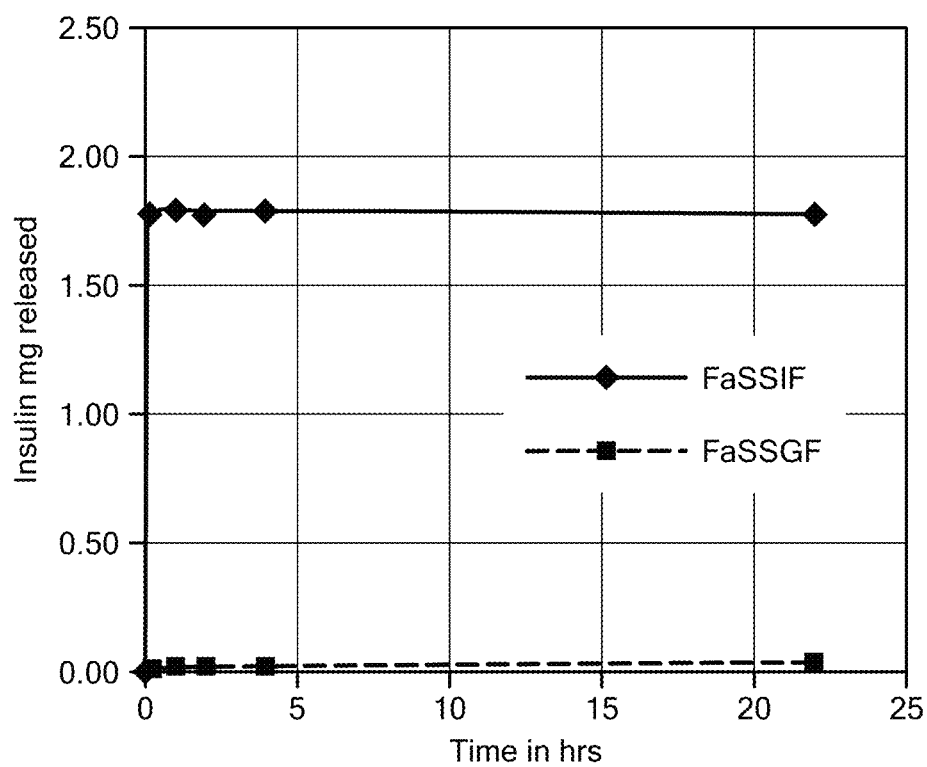
FIG. 16 shows the time course of insulin release from an insulin formulation in FaSSGF and FaSSIF using HPLC.

Formulation 16, containing oleic acid as permeability enhancer, had a mean particle size of 18.55 nm as measured by DLS (FIG. 14). One ml aliquots were distributed in two 20 mL vials and lyophilized. One vial was reconstituted with FaSSGF, and the pH was adjusted to less than 2.0. The second vial was reconstituted with FaSSIF at pH 6.5. Insulin release profile was monitored for 24 hours. At each time point, the samples were centrifuged at 10,000 rpm for 5 minutes and the supernatant was assayed for its insulin content by ELISA and HPLC. FIGS. 15 and 16 show the release profile. Insulin was released into the supernatant only at pH 6.5 and not at acidic pH of less than 2.0 with the inclusion in the nanoparticles of oleic acid.

Example 9

Treatment of Diabetes with Oral Insulin Formulation

The efficacy of the formulation prepared by the solvent-based method was tested on a human subject who had type 2 diabetes and was taking a daily dose of 100 mg of metformin and 42 units of insulin at night. This medication protocol was considered as the positive control. For the negative control, the medication was stopped altogether for a day.

Figure 17:
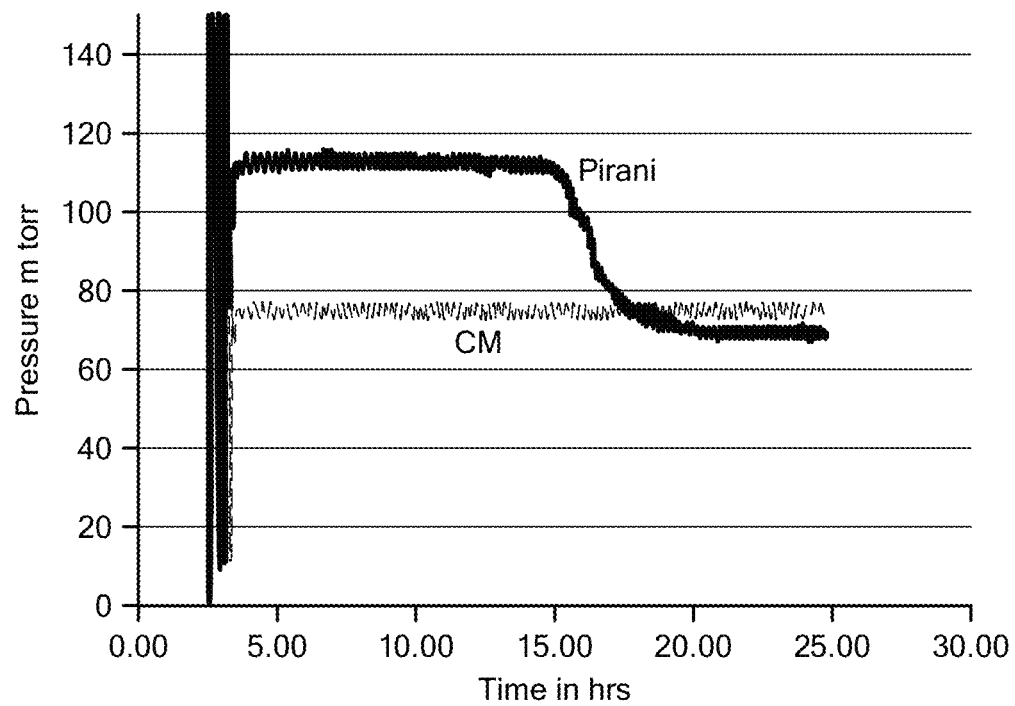
FIG. 17 shows a lyophilization pressure profile.
Figure 18:
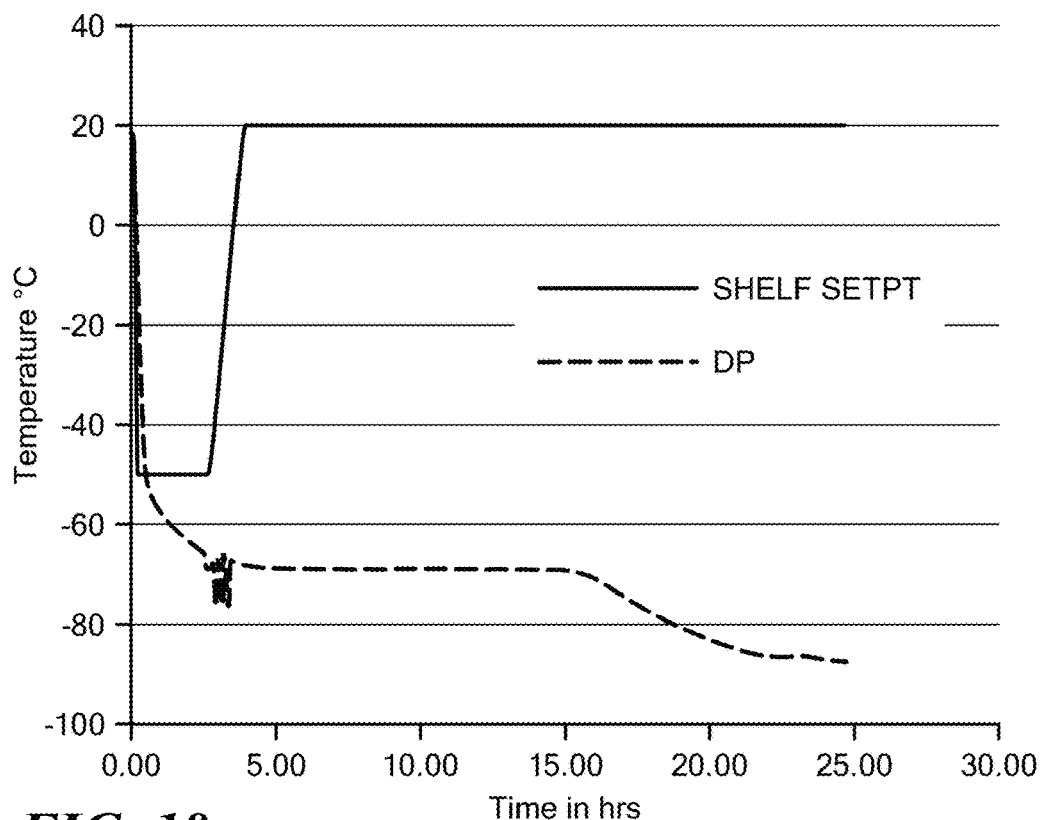
FIG. 18 shows a lyophilization temperature profile.

The nanoparticle formulation was prepared as follows. 212 mg of insulin was weighed in a 150 mL beaker, followed by the addition of 5 mL of 0.01N HCl to dissolve the insulin. Then, 1.072 g of EUDRAGIT L 100 in ethanol was added, followed by 105 mL of pH 6.5 buffer. The pH of the mixture was 5.71; it was then adjusted either to 5.95 using 5N NaOH (to yield Formulation 16) or to pH 3.3 using HCl (to yield Formulation 17). 16 mL of each formulation was dosed into 6 50-mL vials, partially stopped with rubber stoppers, and lyophilized. The completion of the lyophilization was considered to be when the pressure measured by the Pirani gauge in contact with the sample reached the shelf set pressure (FIGS. 17 and 18). The formulations were then reconstituted with 15 mL of water for injection to obtain a final concentration of 2 mg/mL. 15 mL of this formulation containing 2 mg/mL of insulin was taken orally by the subject, one formulation per night. All medications were taken immediately after a meal. Blood sugar levels were measured using a OneTouch Ultra® glucose meter with OneTouch Ultra® test strips (LifeScan, Inc.) two hours after the meal. The first reading was considered time 0. The data indicated that while glycemia steadily decreased after administration of metformin and insulin (positive control), blood sugar level was higher than 200 mg/dl in the absence of medication (negative control). The experimental data showed that oral administration of either Formulation 17

Figure 19:
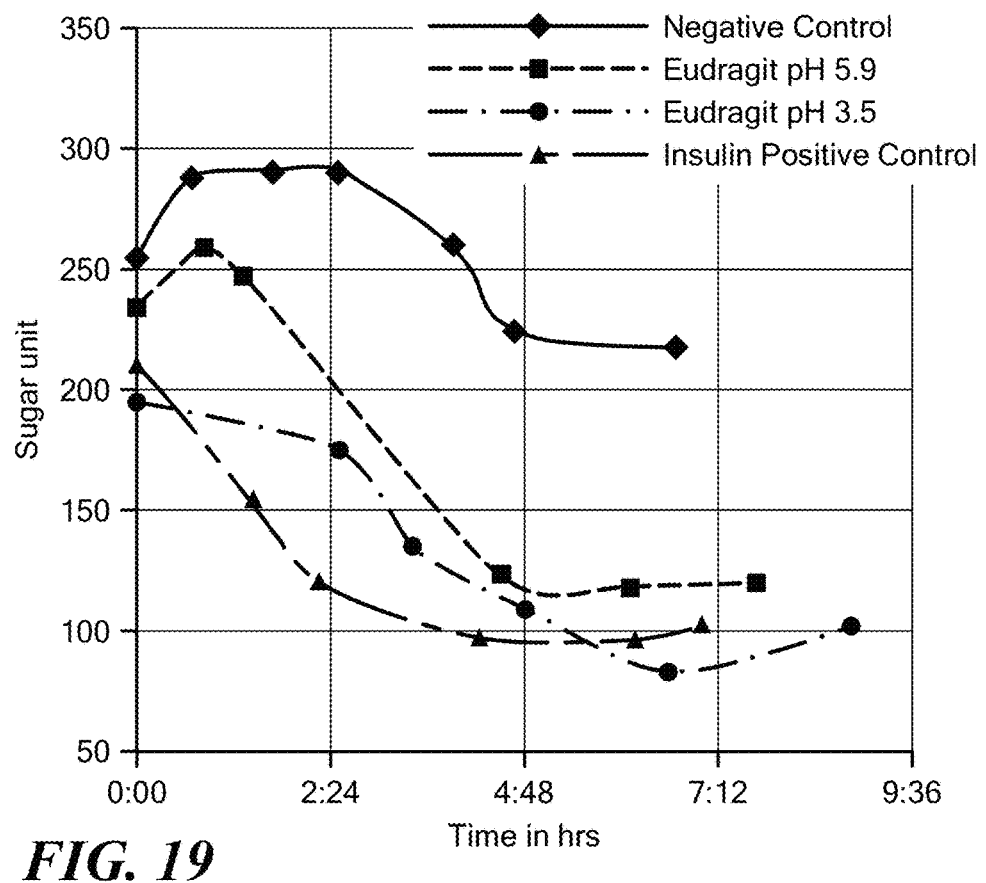
FIG. 19 shows changes in postprandial blood glucose of a human subject in response to administration of insulin formulations and to controls.

(pH 5.9) or Formulation 18 (pH 3.5) was able to reduce postprandial glycemia. Starting at about hour 2, blood sugar level decreased steadily to normoglycemic levels (about 100 mg/dl) (FIG. 19).

Example 10

Control of Blood Glucose with Oral Insulin Formulation

An experiment was conducted to compare the blood glucose response in dogs to a single oral dose of EUDRAGIT L100-Insulin (Formulation 16) to that of a single subcutaneous injection of commercial HUMULIN R insulin (Lilly, USA).

Figure 20:
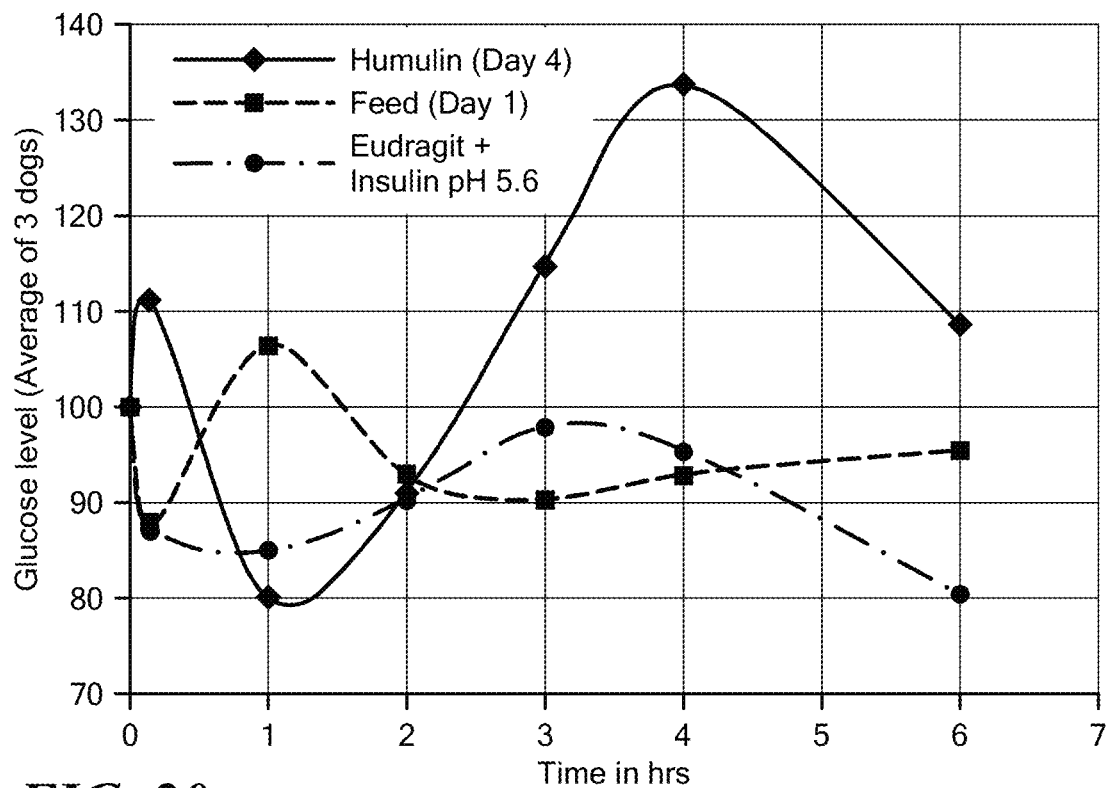
FIG. 20 shows the mean normalized blood glucose of 3 dogs after administration of various insulin formulations.

Three non-naïve female beagle dogs were administered a single 2-mg/kg dose of Formulation 16 in sterile water for injection USP by oral gavage on Day 2 and a single 0.5 U/kg dose of HUMULIN R Insulin by subcutaneous injection on Day 4. Blood glucose levels were measured on Day 1 just prior to feeding, immediately after food removal, and 1, 2, 3, 4, and 6 hours after food removal. On Day 2 and Day 4, blood glucose levels were measured just prior to feeding, immediately after food removal but before dosing, and 1, 2, 3, 4, 6, and 24 hours post dose (prior to feeding). Animals were returned to stock after the completion of study data collection on Day 5. The study design is shown in Table 3. There was no mortality and no test article-related clinical observations or adverse effects noted in the dogs. The results are shown in FIG. 20.

The glycemia of the three dogs after oral administration of the oral insulin formulation ranged from 80-98% of control glucose levels 6 hours after feeding. In contrast, the subcutaneous administration of HUMULIN resulted in 80-134% of control glucose levels, thus suggesting prolonged maintenance of lower glycemia after oral administration of the nanoparticle insulin formulation compared to subcutaneous administration of HUMULIN. Oral administration of Formulation 16 resulted in normalized blood glucose levels for two of the three dogs within 2 hours postdose. Administration of HUMULIN resulted in lower glycemia within 1 hour postdose, but higher glycemia 3-6 hours postdose (120% to 174% of control values) when compared to Day 1 (non-dosed) values. These observations suggest that oral administration of the nanoparticle-insulin formulation better mimics the effect of endogenous insulin in the body after secretion, providing a better glucose homeostasis. Overall, blood glucose levels were lower and more stable (fewer fluctuations) following oral administration of Formula 16 than after subcutaneous administration of HUMULIN.

TABLE 3

Design of Dog Insulin Study

| Number of Dogs | Day | Insulin Formulation | Route of Administration | Insulin Dose | Insulin Concentration | Dose Volume (mL/kg) |
|---|---|---|---|---|---|---|
| 3 | 2 | Formulation 16 | Oral Gavage | 2 mg/kg | 2 mg/mL | 1 |
|   | 4 | HUMULIN R Insulin | Subcutaneous Injection | 0.5 Units/kg | 100 Units/mL | 0.005 |

Example 11

Preparation of Anti-EGFR Antibody Oral Formulation by the Solvent-Free Method

ERBITUX (cetuximab) is an epidermal growth factor receptor (EGFR) antagonist indicated for the treatment of head and neck cancer and colorectal cancer. The recommended initial dose is 400 mg/m$^2$ administered as a 120-minute intravenous infusion (maximum infusion rate 10 mg/min). Cetuximab is commercialized as a 5 mg/mL solution containing 8.48 mg/mL sodium chloride, 1.88 mg/mL sodium phosphate dibasic heptahydrate, 0.41 mg/mL sodium phosphate monobasic monohydrate, and water for injection, USP. 400 µL of cetuximab in this dosage form was added to 20 mg EUDRAGIT L 100 in a 10 mL vial, followed by 2 mL of pH 6.5 buffer (Table 4).

Figure 21:
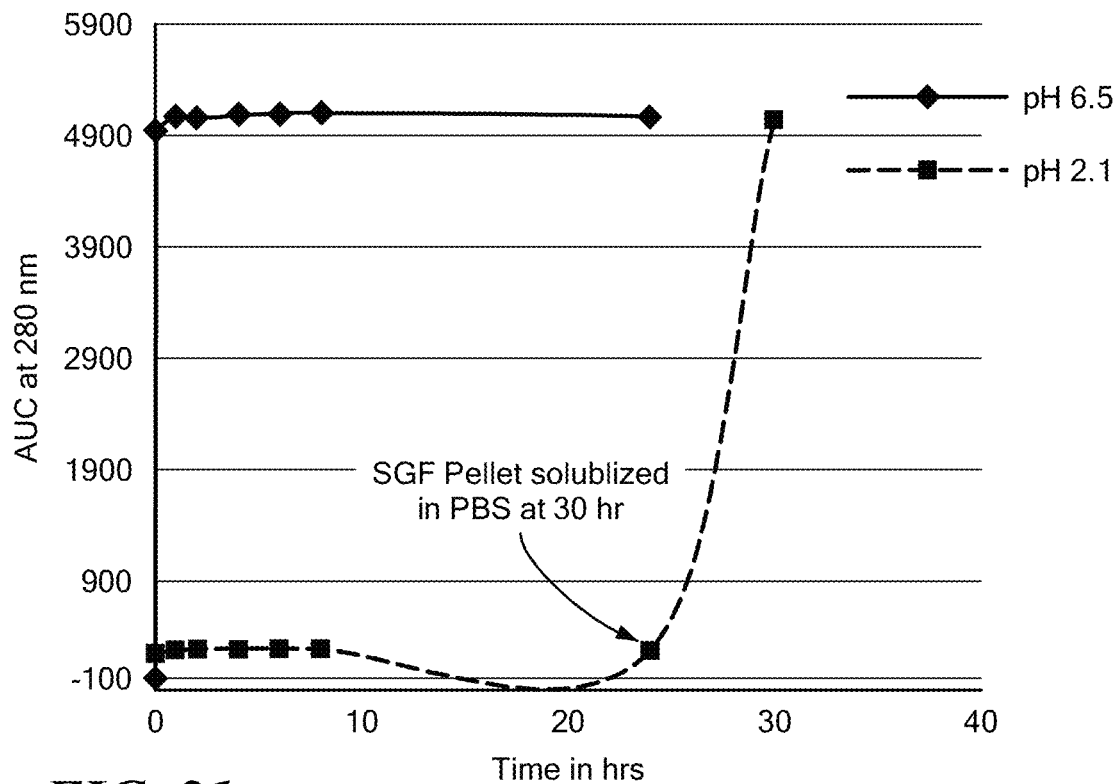
FIG. 21 shows the release profile of anti-EGFR antibody in pH 2.1 and pH 6.5 using size exclusion (SEC) HPLC.

This solution was aliquoted in 1.2 mL samples which were placed in 10 mL vials and lyophilized. One sample was reconstituted with 1 mL of FaSSGF and the second sample was reconstituted with 1 mL of FaSSIF. 120 µL samples were taken at 0, 1, 2, 4, 8 and 24 hours, placed in 1.5 mL centrifuge tubes and centrifuged at 10,000 rpm for 5 minutes. 40 µL of the supernatant of each sample was injected for size-exclusion chromatography—HPLC analysis. SEC-HPLC was conducted using a Tosohaas G3000SWXL column. The release profile indicated that cetuximab was not released into the supernatant in FaSSGF (acidic pH), but was released into the supernatant in FaSSIF (pH 6.5) (FIG. 21). After centrifugation of the 24 hour FaSSGF sample, the pellet was reconstituted with 1 mL of PBS at pH 7.4, whereupon the antibody was released into the supernatant.

TABLE 4

Composition of ERBITUX (Cetuximab) (1 mL, final pH 6.5)

| Component | Concentration/Amount |
|---|---|
| Sodium taurocholate | 2.5 mM |
| Lecithin | 0.6 mM |
| Sodium dihydrogen phosphate | 23.6 mM |
| Sodium chloride | 88.2 mM |
| Sodium hydroxide | 7.2 mM |
| EUDRAGIT L 100 | 10 mg |
| ERBITUX | 1 mg |
| Sodium chloride | 1.4 mM |
| Sodium phosphate dibasic heptahydrate | 0.3 mM |

Example 12

Figure 22:
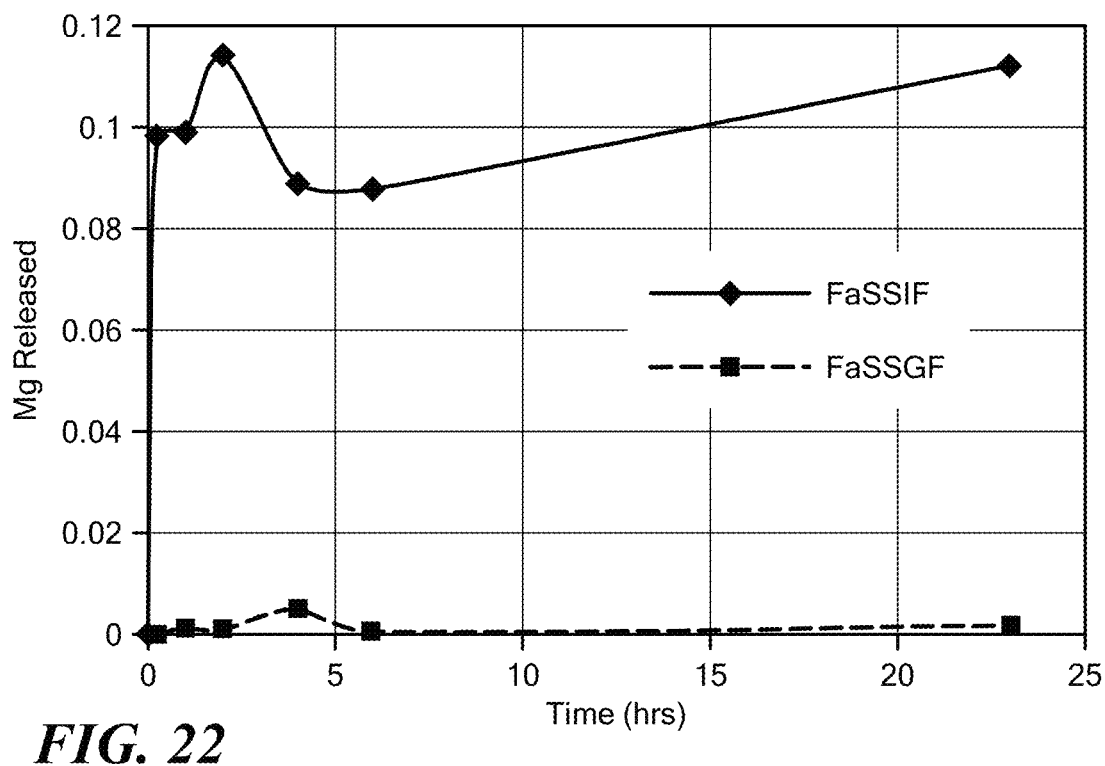
FIG. 22 shows the release profile of anti-Her2 antibody in FaSSGF and FaSSIF using ELISA.

Preparation of Anti-Her-2 Antibody Oral Formulation by the Solvent-Free Method HERCEPTIN (trastuzumab) is indicated for adjuvant treatment of breast cancer. Trastuzumab is a sterile, white to pale yellow, preservative-free lyophilized powder for intravenous administration. Each commercial multi-use vial of trastuzumab contained 440 mg trastuzumab, 400 mg α,α-trehalose dihydrate, 9.9 mg L-histidine HCl, 6.4 mg L-histidine, and 1.8 mg polysorbate 20, USP in lyophilized form. Reconstitution with 20 mL of water for injection yielded a solution containing 21 mg/mL trastuzumab, at a pH of approximately 6.0. For this study, 200 µL of the commercial dosage form of trastuzumab was added to 70 mg EUDRAGIT L 100 in a 10 mL vial. To this solution, 7.5 mL of pH 6.5 buffer was added. Then, 1.45 mL aliquots of the solution were placed in 10 mL vials and lyophilized. One sample was reconstituted with 1 mL of FaSSGF at pH 2.1 and the second sample was reconstituted with FaSSIF at pH 6.5. 120 µL samples were taken at 0, 1, 2, 4, 8, and 24 hours, placed in 1.5 mL centrifuge tubes and centrifuged at 10,000 rpm for 5 minutes. The activity of the recovered trastuzumab was evaluated with a functional ELISA assay. To this end, after reconstitution with FaSSGF (pH 1.5-2) or FaSSIF (pH 6.5), the final pH was adjusted to pH 1.5 and 6.5 respectively, due to the buffering capacity of trastuzumab formulation buffer. The samples were then diluted 20,000 fold with the ELISA assay buffer. Detection and quantification of trastuzumab was then conducted using Human IgG total Ready-Set-Go!® kits (Affymetrix/eBioscience Inc., San Diego, Calif., USA). No release of trastuzumab into the supernatant at acidic pH was observed even after 24 hours. However, at pH 6.5, most of the antibody was released into the supernatant within 1 hour (FIG. 22).

TABLE 5

Composition of HERCEPTIN (Trastuzumab) (1 mL, final pH 6.5).

| Component | Concentration/Amount |
|---|---|
| Sodium taurocholate | 2.9 mM |
| Lecithin | 0.7 mM |
| Sodium dihydrogen phosphate | 27.6 mM |
| Sodium chloride | 103.1 mM |
| Sodium hydroxide | 8.5 mM |
| EUDRAGIT L 100 | 10 mg |
| HERCEPTIN | 1 mg |
| Trehalose | 0.519 mM |
| Histidine HCl | 0.013 mM |
| Histidine | 0.008 mM |
| Polysorbate 20 | 0.002 mM |

Example 13

Figure 23:
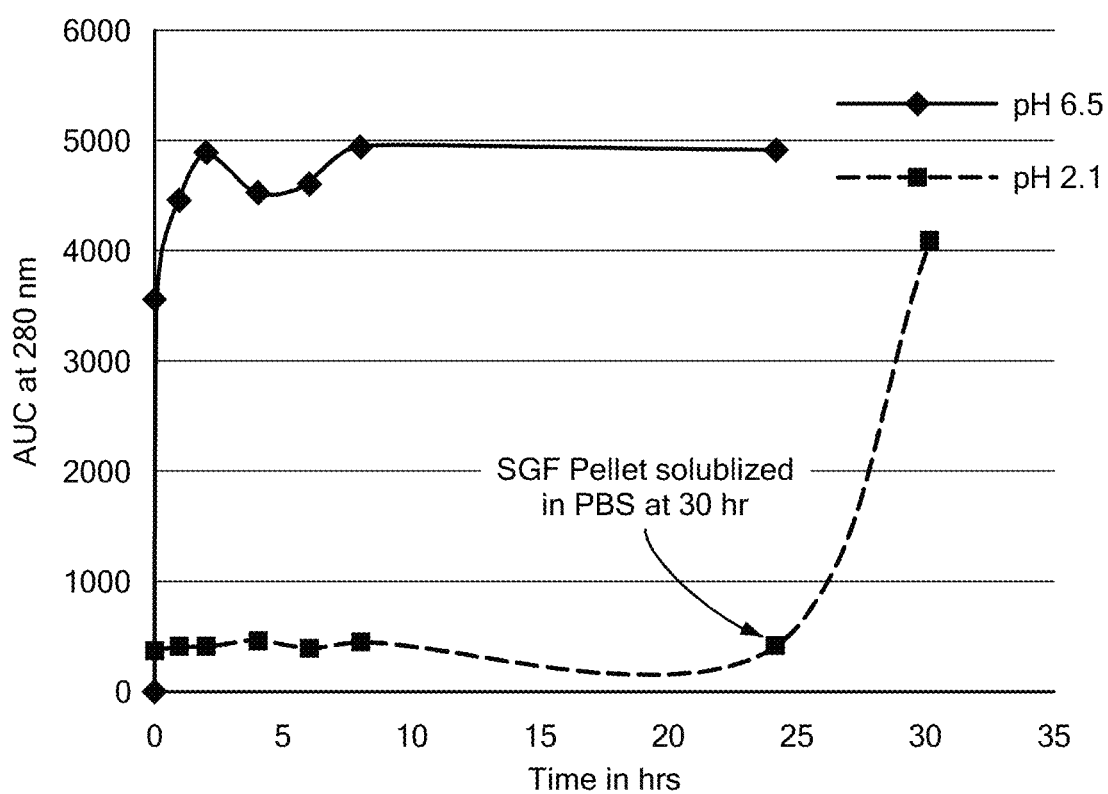
FIG. 23 shows the release profile of anti-RSV antibody in pH 2.1 and pH 6.5 using SEC-HPLC.
Figure 24:
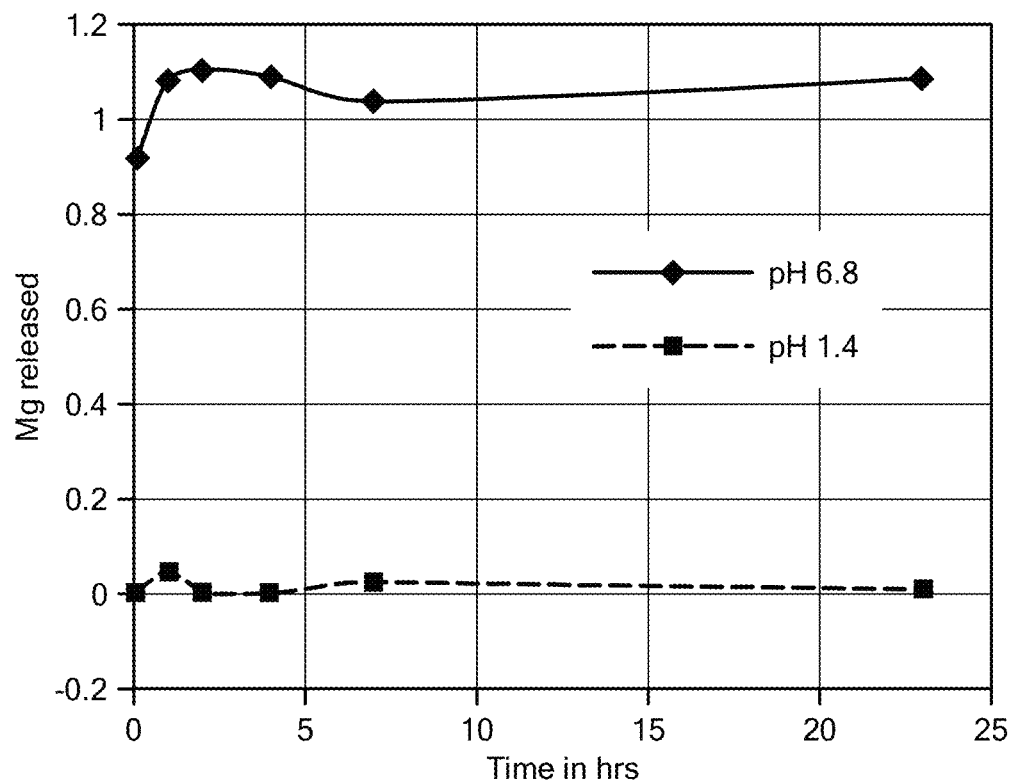
FIG. 24 shows the release profile of anti-RSV antibody in pH 2.1 and pH 6.5 using ELISA.

Preparation of Anti-RSV Antibody Oral Formulation by the Solvent-Free Method SYNAGIS (palivizumab) is a humanized monoclonal antibody (IgGlk) produced by recombinant DNA technology, directed to an epitope in the A antigenic site of the F protein of respiratory syncytial virus (RSV). Each 100 mg single-dose vial of palivizumab liquid solution contains 100 mg of palivizumab, 3.9 mg of histidine, 0.1 mg of glycine, and 0.5 mg of chloride in a volume of 1 mL at a pH of approximately 6.0. The dosage form is an intramuscular injection. 98 µL of palivizumab was added to 98 mg EUDRAGIT L 100 in a 10 mL vial. To this solution, 9.8 mL of the pH 6.5 buffer was added. Then, two 1.1 mL samples were placed in 10 mL vials and lyophilized. One sample was reconstituted with 1 mL of FaSSGF (pH 2.1) and the second sample was reconstituted with 1 mL FaSSIF (pH 6.5). 120 µL samples were taken at 0, 1, 2, 4, 8, and 24 hours, placed in 1.5 mL centrifuge tubes and centrifuged at 10,000 rpm for 5 minutes. 40 µL of the supernatant of each sample was injected for SEC-HPLC analysis, which was conducted using a Tosohaas G3000SWXL column. No release of trastuzumab was observed at acidic pH even after 24 hours. However, complete release of this antibody was observed in FaSSIF at pH 6.5. After centrifugation of the 24 hour FaSSGF sample, the pellet was reconstituted with 1 mL of PBS at pH 7.4. Palivizumab was only released when the solution reached neutral pH, even after being kept in acidic medium for 24 hours (FIG. 23). In addition to SEC data, antibody activity was assessed with a functional ELISA assay. To this end, after reconstitution with FaSSGF or FaSSIF, the final pH was adjusted to pH 1.5 and 6.5, respectively. The samples were then diluted 20,000 fold with the ELISA assay buffer. Detection and quantification of palivizumab was then conducted using Human IgG total Ready-Set-Go!® kits (Affymetrix/eBioscience Inc., San Diego, Calif., USA). No release of palivizumab into the supernatant at acidic pH was observed even after 24 hours. However, at pH 6.5, most of the antibody was released into the supernatant within 1 hour (FIG. 24).

TABLE 6

Composition of SYNAGIS (Palivizumab) (1 mL, final pH 6.5).

| Component | Concentration/Amount |
|---|---|
| Sodium taurocholate | 2.7 mM |
| Lecithin | 0.67 mM |
| Sodium dihydrogen phosphate | 25.00 mM |
| Sodium chloride | 95.00 mM |
| Sodium hydroxide | 7.9 mM |
| EUDRAGIT L 100 | 10 mg |
| SYNAGIS | 1 mg |
| Histidine | 0.39 mM |
| Glycine | 0.01 mM |

Example 14

Preparation of Anti-TNF-Antibody Oral Formulation by the Solvent-Free Method HUMIRA (adalimumab) is a tumor necrosis factor (TNF) blocker indicated for treatment of rheumatoid arthritis, psoriatic arthritis, ankylosing spondylitis, Crohn's disease, and plaque psoriasis. Adalimumab is supplied as a sterile, preservative-free solution of adalimumab for subcutaneous administration. The drug product is supplied as either a single-use, prefilled pen or as a single-use, 1 mL prefilled glass syringe. Enclosed within the pen is a single-use, 1 mL prefilled glass syringe. The solution of adalimumab is clear and colorless, with a pH of about 5.2. Each syringe delivers 0.8 mL (40 mg) of drug product. Each 0.8 mL of this dosage form contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for injection USP. Sodium hydroxide is added as necessary to adjust pH. This dosage form is for intramuscular injection. The formulation was diluted to 1 mg/mL with the respective formulation buffer. Two mL of adalimumab was added to 20 mg EUDRAGIT L 100 in a 10 mL vial. 1.0 mL samples of this solution were placed in 10 mL vials and lyophilized.

Figure 25:
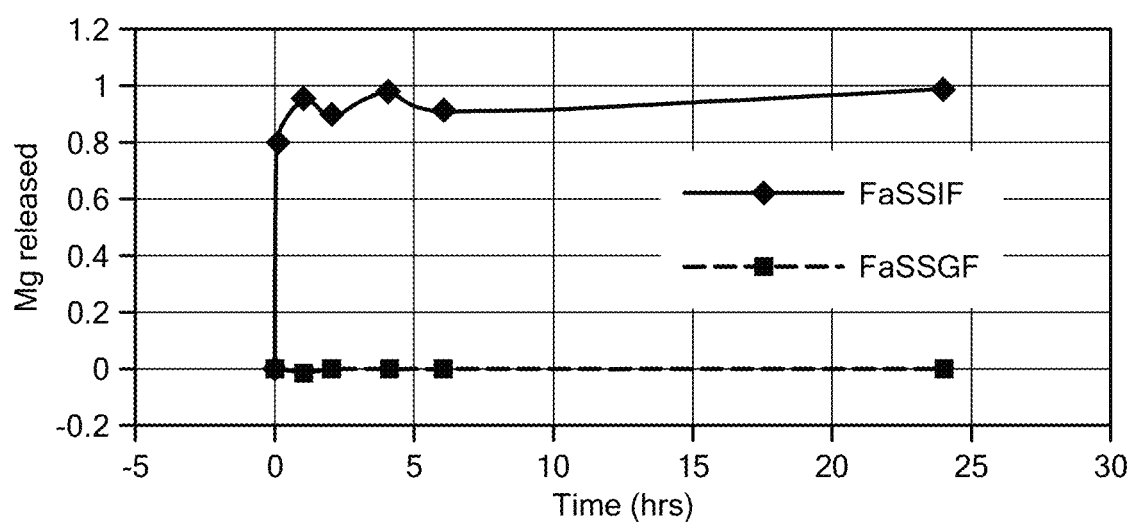
FIG. 25 shows the release profile of anti-TNF antibody in pH 2.1 and pH 6.5 using ELISA.

One sample was reconstituted with 1 mL of FaSSGF (pH 2.1) and the second sample was reconstituted with 1 mL of FaSSIF (pH 6.5). 120 μL samples were taken at 0, 1, 2, 4, 8, and 24 hours, placed in 1.5 mL centrifuge tubes and centrifuged at 10,000 rpm for 5 minutes. The supernatant was assayed for its activity against TNF using a functional ELISA assay. To this end, each sample was diluted 10,000 fold with either FaSSGF or FaSSIF and further diluted 6 fold with dilution sample buffer from the kit Adalimumab (HU-MIRA) ELISA Assay Kit (Eagle Biosciences, Inc., Nashua, N.H., USA). There was no release of adalimumab into the supernatant in the acidic medium even after 24 hrs. However, at pH 6.5, most of the antibody was released into the supernatant within 1 hour (FIG. 25).

TABLE 7

Composition of HUMIRA (Adalimumab) (1 mL, final pH 6.5).

| Component | Concentration/Amount |
|---|---|
| EUDRAGIT L 100 | 10 mg |
| HUMIRA | 1 mg |
| Sodium chloride | 6.2 mM |
| Monobasic sodium phosphate | 0.9 mM |
| Monobasic sodium phosphate dihydrate | 1.5 mM |
| Sodium citrate | 0.24 mg |
| Citric acid monohydrate | 1.3 mM |
| Mannitol | 12.0 mM |

Example 15

Preparation of Anti-IL-6 Antibody Oral Formulation by the Solvent-Free Method

ACTEMRA (tocilizumab) is an interleukin-6 (IL-6) receptor antagonist indicated for treatment of: rheumatoid arthritis, polyarticular juvenile idiopathic arthritis, and systemic juvenile idiopathic arthritis. It is commercialized as a single-use prefilled glass syringe providing 162 mg of antibody in 0.9 mL. Inactive ingredients are L-arginine, L-arginine hydrochloride, Lmethionine, L-histidine, L-histidine hydrochloride monohydrate. This dosage form is for subcutaneous injection. For this study, the formulation was diluted to 2 mg/mL with the respective formulation buffer. One mL of tocilizumab was added to 20 mg EUDRAGIT L 100 in a 10 mL vial, and then one ml the pH 6.5 buffer was added. The pH was then adjusted to 6.8. 1.0 mL samples of the solution were placed in 10 mL vials and lyophilized.

Figure 26:
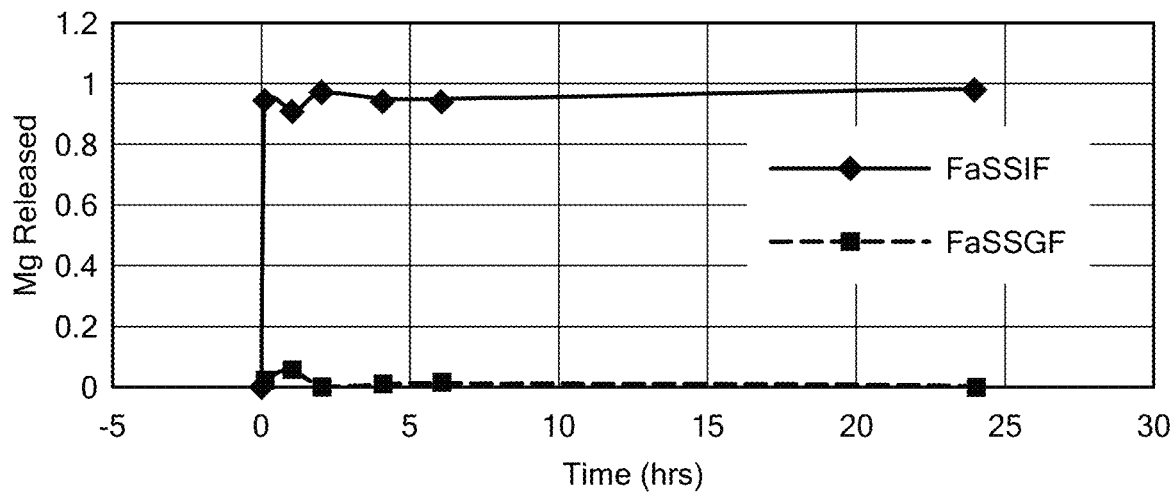
FIG. 26 shows the release profile of anti-IL6 antibody in pH 2.1 and pH 6.5 using ELISA.

One sample was reconstituted with 1 mL of FaSSGF (pH 2.1), and a second sample was reconstituted with 1 mL of FaSSIF (pH 6.5). 120 μL samples were taken at 0, 1, 2, 4, 8, and 24 hours, placed in 1.5 mL centrifuge tubes and centrifuged at 10,000 rpm for 5 minutes. The activity of the recovered tocilizumab was evaluated with a functional ELISA assay. To this end, after reconstitution with FaSSGF (pH 1.5-2.0) or FaSSIF (pH 6.5), the final pH was adjusted to pH 1.5 and 6.5, respectively. The samples were then diluted 20,000 fold with the ELISA assay buffer. Detection and quantification of tocilizumab was then conducted using Human IgG total Ready-Set-Go!® kits (Affymetrix/eBio-science Inc., San Diego, Calif., USA). No release of tocilizumab into the supernatant in acidic pH was observed even after 24 hours. However, at pH 6.5, most of the antibody was released into the supernatant within 1 hour (FIG. 26).

TABLE 8

Composition of ACTEMRA (tocilizumab) (1 mL composition) Lyophilized

| Component | Concentration/Amount |
|---|---|
| Sodium taurocholate | 1.5 mM |
| Lecithin | 0.375 mM |
| Sodium dihydrogen phosphate | 14.18 mM |
| Sodium chloride | 52.93 mM |
| HCl | to adjust pH to 6.5 |
| Sodium hydroxide | 4.35 mM |
| EUDRAGIT L 100 | 10 mg |
| ACTEMRA | 1 mg |
| Polysorbate-80 | 0.1 mM |
| Arginine | 73.3 mM |
| Arginine HCl | 10.4 mM |
| Methionine | 2.2 mM |
| Histidine | 0.8 mM |

Example 16

Preparation of Ascorbic Acid Oral Formulation by the Solvent-Free Method 10 mL of an ascorbic acid solution was prepared with the following composition:
1.75 g ascorbic acid
100 mg Eudragit
1.75 g soy lecithin
2.7 mM sodium taurocholate
0.7 mM soy lecithin
28.36 mM monobasic sodium phosphate,
105.85 mM sodium chloride
1N NaOH to pH 6.5

One ml of the above formulation was dialyzed against 100 mL of FASSIF at pH using a 100 Kda cutoff dialysis membrane to test the release profile at intestinal condition. One ml of a second aliquot was adjusted to pH 2.0 and dialyzed against 100 mL of FASSGF at pH 1.5 to test the release profile at gastric condition. The aliquots of the samples were taken at different time point and the ascorbic acid content was measured at 260 nm using a Molecular Device UV-VIS spectrophotometer after 100-fold dilution with respective FASSIF or FASSGF solution. Ascorbic acid dissolved in FASSIF at pH 6.5 was used as standard. FASSIF or FASSGF was used as blank.

Figure 27:
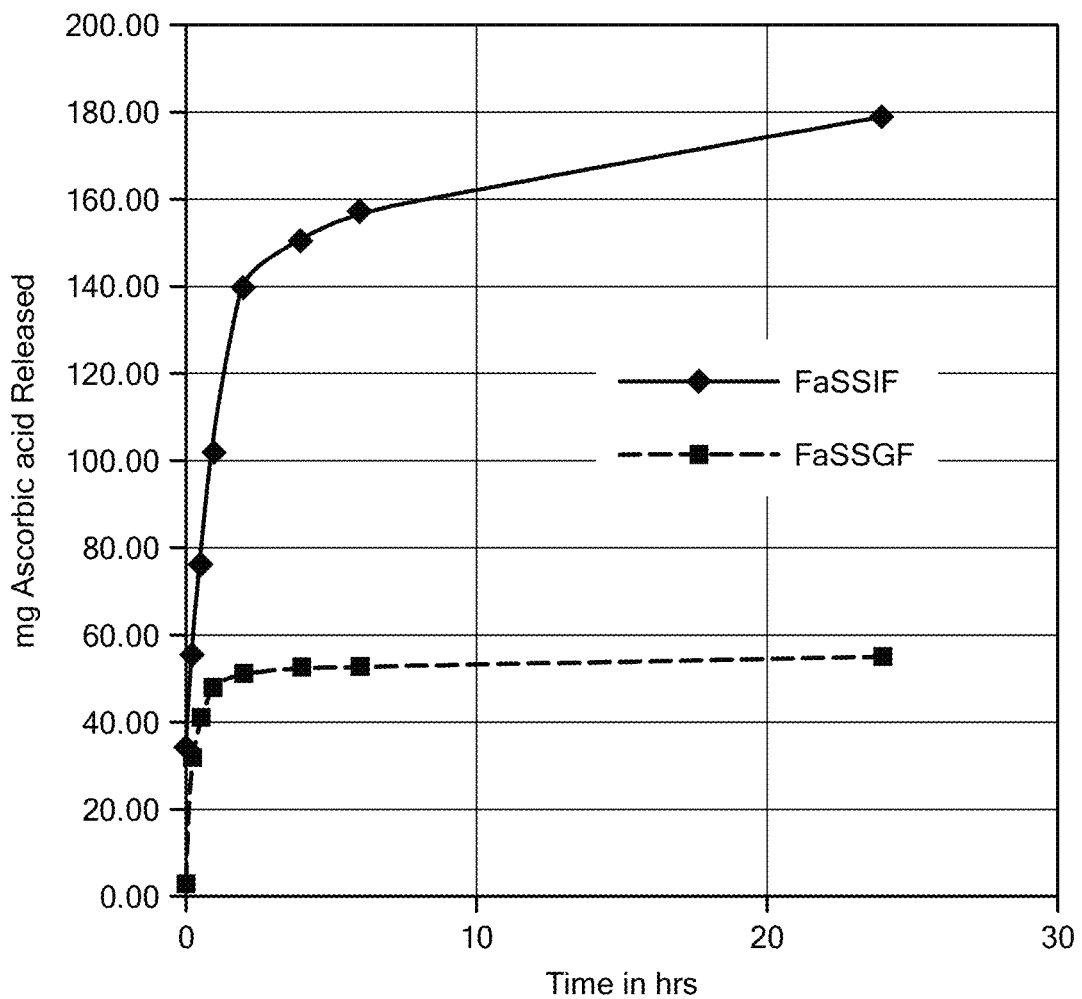
FIG. 27 shows the release profile of ascorbic acid in FASSIF and FASSIF measured spectrophotometrically using A280.
Figure 28:
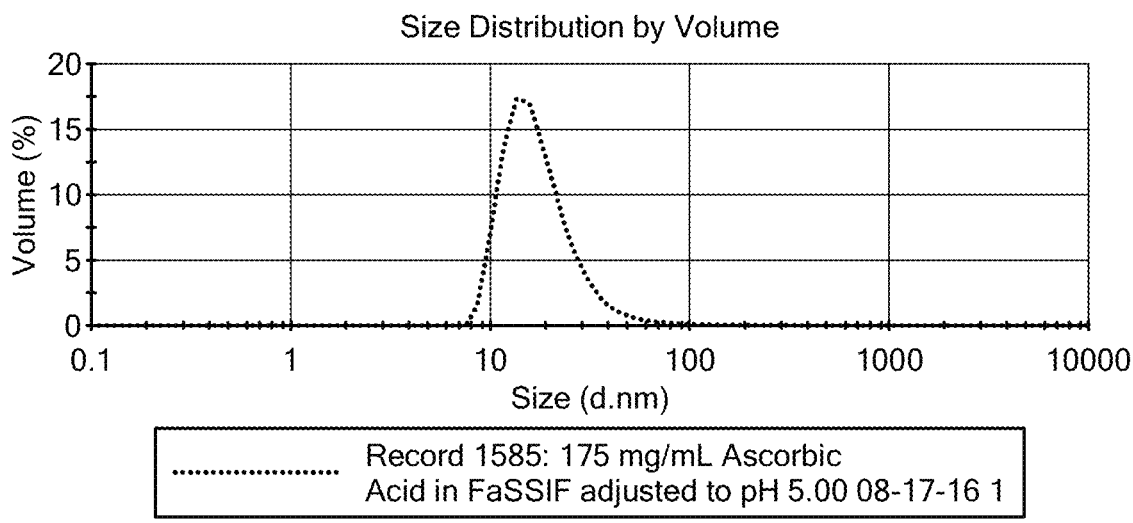
FIG. 28 shows measurement of particle size of ascorbic acid-containing nanoparticles using DLS.

The data (see FIG. 27) indicated that ascorbic acid is released only at pH 6.5 and not significantly released at very acidic pH The mean particle size of the final formulation by DLS was 34.9 nm (FIG. 28). The results suggest that the formulation is useful for oral delivery of vitamin C, providing a high load of 175 mg/mL. The formulation is easily lyophilizable and can be delivered as a powder for suspension, tablet, or capsule, or can be delivered as a stable aqueous suspension for pediatric formulation.

Example 17

Figure 29:
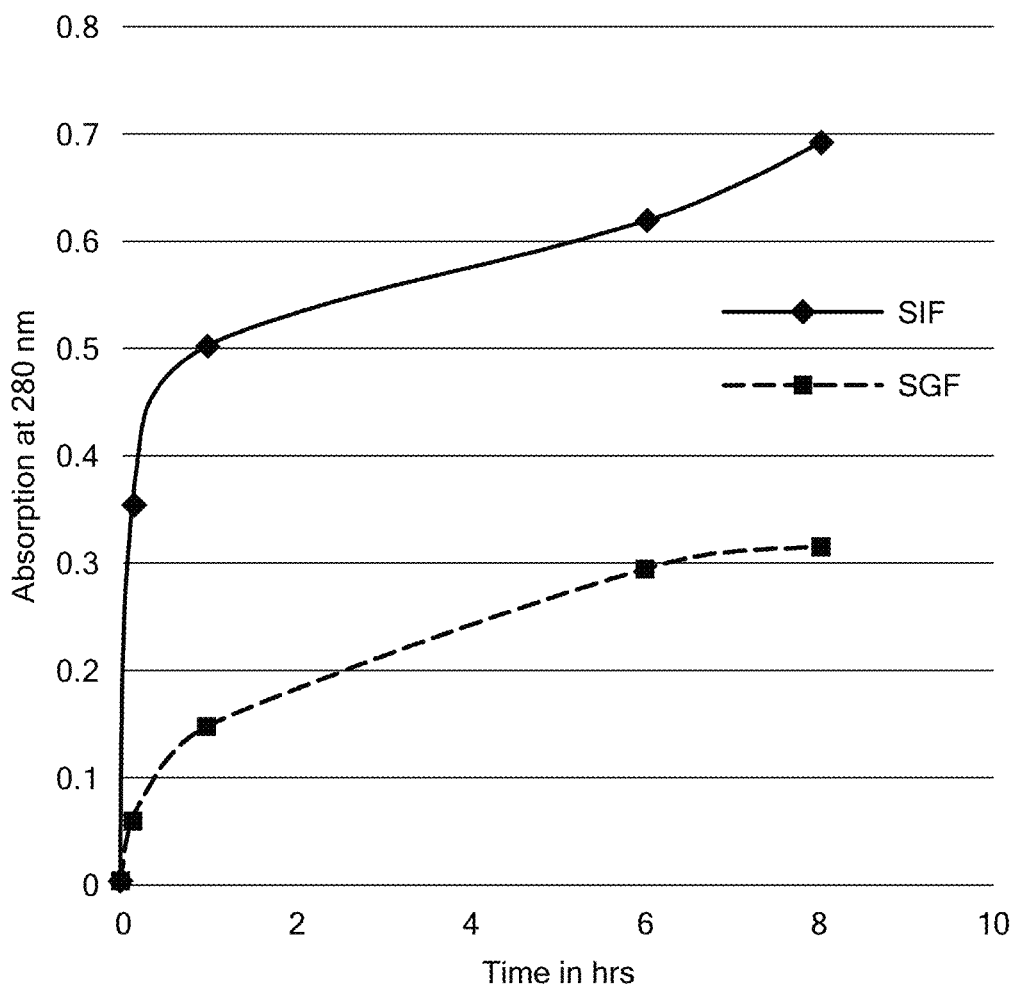
FIG. 29 shows the release profile of albumin encapsulated by the solvent-based method.

Preparation of Bovine Serum Albumin-Containing Nanoparticles by the Solvent-Based Method 1 mL of 10 mg/mL bovine serum albumin was diluted into 10 mL 1% EUDRAGIT L 100 in ethanol. The samples were kept at −20° C. for 30 minutes and then centrifuged at 3200 rpm. The pellet was dried overnight and reconstituted in 1 mg/mL of either FaSSGF (pH 1.5-2.0) or FaSSIF (pH 6.5). The release profiles shown in FIG. 29 indicate that the albumin was released into the supernatant rapidly at neutral pH (FaSSIF) and only slowly at acidic pH (FaSSGF).

Example 18

Preparation of Insulin Nanoparticles by the Solvent-Based Method

Figure 30:
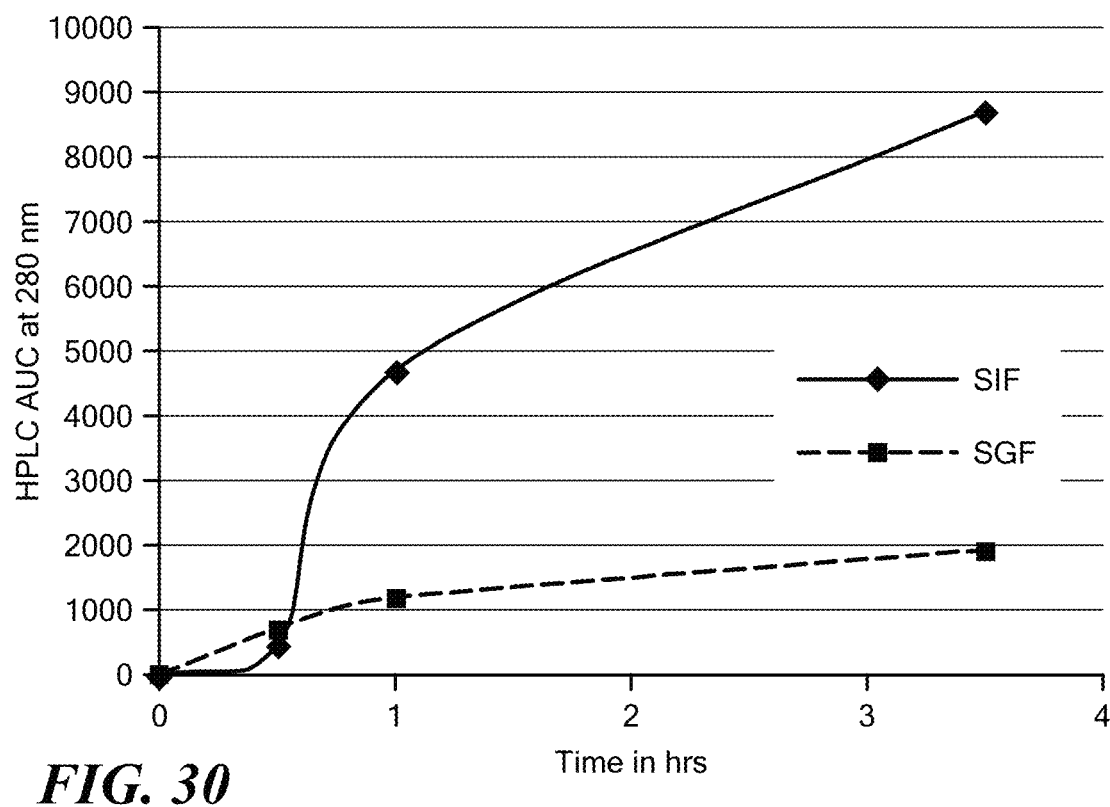
FIG. 30 shows the time course of insulin release from an insulin encapsulated by the solvent-based method.

It is known that insulin is soluble at acidic pH but not at neutral pH. 10 mg/mL insulin solution was prepared by first dissolving insulin in 0.01N HCl. When 0.1 mL of the insulin solution was added to 1 mL of 2% EUDRAGIT L 100 in ethanol, there was no visible precipitation, indicating that at acidic pH insulin is soluble even at 90% of organic solvent. When the formulation was neutralized with 0.1N NaOH, insulin and EUDRAGIT co-precipitated. The precipitate contained nanoparticles with a Z average particle size of about 1110 nm. The samples were kept at −20° C. for 30 minutes and then centrifuged at 3200 rpm. The pellet was dried for 2 hours using a vacuum centrifuge and tested for release profile in FaSSGF and FaSSIF. The data shown in FIG. 30 indicate that insulin was released into the supernatant preferably at neutral pH.

Example 19

Figure 31:
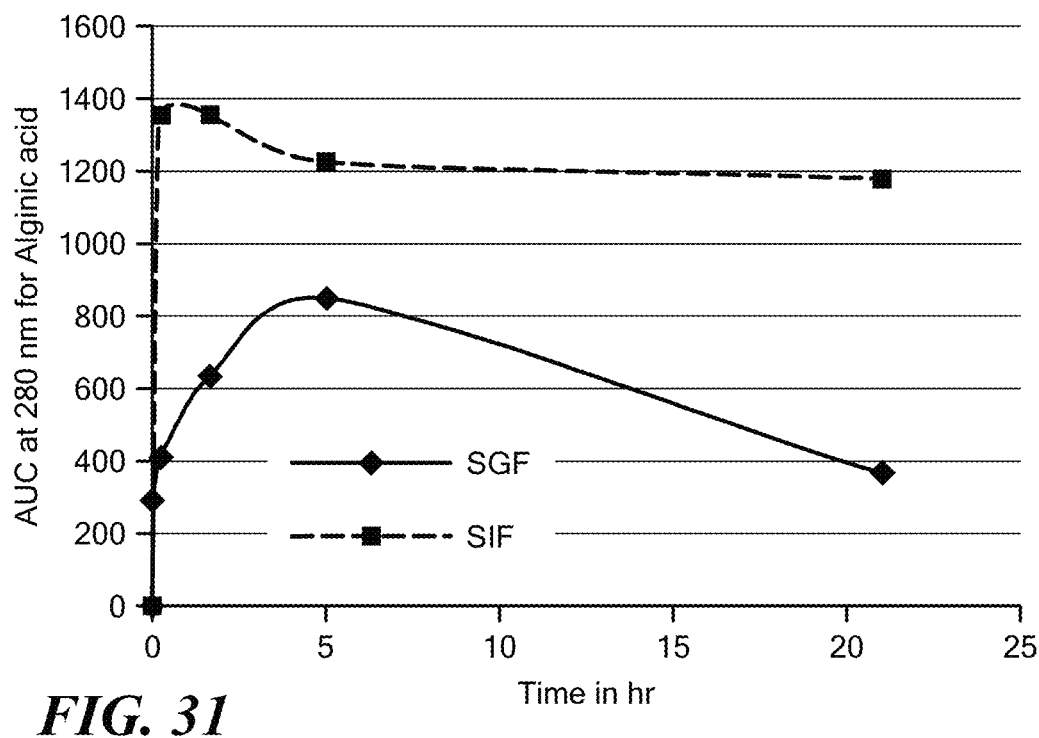
FIG. 31 shows the time course of insulin release from a nanoparticle formulation containing insulin and 2% alginic acid encapsulated by the solvent-based method.

Preparation of Insulin-Alginic Acid-Containing Nanoparticles by the Solvent-Based Method 100 µL of 2% alginic acid in water was added to 1 mL of 1% EUDRAGIT L 100 in ethanol and vortexed. 10 mg/mL insulin was prepared by dissolving insulin in 0.01N HCl. Subsequently, 0.1 mL of 10 mg/mL insulin in 0.01N HCl was added to the ethanol solution. No visible precipitation occurred. However, when the formulation was neutralized with 0.1N NaOH, the insulin and EUDRAGIT co-precipitated. The samples were kept at −20° C. for 30 minutes and then centrifuged at 3200 rpm. The pellet was dried for 2 hours using a vacuum centrifuge and tested for insulin release in FaSSGF and FaSSIF. The data are shown in FIG. 31, and indicate that insulin was released preferentially into the supernatant at neutral pH.

Example 20

Association of Insulin with Eudragit Nanoparticles

Insulin-containing nanoparticles were formed by the solvent-free method as follows. A formulation having the following composition was prepared:
  1 mL 20 mg/ml insulin stock
  100 mg Eudragit L-100
  100 uL 0.2N NaOH to pH 6.5
  2.7 mM sodium taurocholate
  0.7 mM soy lecithin
  28.36 mM monobasic sodium phosphate
  105.85 mM sodium chloride
The formulation had a particle size of 18 nm based on DLS analysis. 1 ml aliquots were distributed in 20 mL vials and lyophilized. One vial was reconstituted with FASSGF and the pH was adjusted to pH 1.6. The resulting suspension was cloudy. The second vial was reconstituted with FASSIF and the pH of the reconstituted solution was pH 5.5. The resulting suspension was white opalescent. A third vial was reconstituted with FASSIF and the pH was adjusted to 6.5. The resulting suspension was clear and transparent. The samples were transferred to dialysis tubings with a molecular weight cutoff of 50,000 Da. The samples were dialyzed against 2 mL of FASSGF pH 1.6, FASSIF pH 5.5, or FASSIF at pH 6.5 and insulin release from the dialysis tubings was monitored at 0, 0.15, 0.30, 1.0, 2.0, 4.0, and 24 hours by RP-HPLC. The HPLC data indicated that insulin remained tightly associated with the nanoparticles at any pH for a period of 24 hrs suggesting. After 24 hrs, the FASSIF pH 6.5 sample was removed from the inside of the dialysis bag and tested for the insulin content by RP-HPLC method. The data indicated that full recovery of 2 mg/mL insulin was seen for the sample inside the dialysis bag.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. An oral formulation of a therapeutic agent, the formulation comprising a plurality of nanoparticles, the nanoparticles comprising a pH-sensitive polymer and a therapeutic agent, the therapeutic agent having a molecular weight from about 1000 to about 10000 Daltons,
   wherein the polymer is insoluble at acidic pH and soluble at neutral or alkaline pH and wherein the pH-sensitive polymer is selected from the group consisting of a copolymer of methacrylic acid and an acrylic or methacrylic ester, methacrylic acid-methylmethacrylate copolymer, methacrylic acid-ethyl acrylate copolymer, a cellulose derivative, cellulose acetate phthalate, cellulose acetate succinate, cellulose acetate trimellitate, hydroxypropyl methylcellulose phthalate, hydroxypropyl methylcellulose acetate succinate, and combinations thereof; wherein a suspension of the nanoparticles is made by a process comprising dissolving the therapeutic agent and suspending the pH-sensitive polymer in an aqueous medium in which the therapeutic agent is soluble and associating the dissolved therapeutic agent and the suspended pH-sensitive polymer in the aqueous medium by adjusting the pH between about 5.5 and about 8 so as to form nanoparticles having a mean particle size of 50 nm or less with mixing alone and without the use of sonication, heat, or any other input of external energy; wherein the therapeutic agent and pH-sensitive polymer do not dissociate from the nanoparticles at acidic pH, with the proviso that the nanoparticles do not contain two different polymers, one polymer present in a core structure and the other polymer present in a shell structure and associated with the therapeutic agent.

2. The formulation of claim 1, wherein the formulation consists essentially of said plurality of nanoparticles suspended in an aqueous medium devoid of organic solvent, wherein the nanoparticles consist essentially of said pH-sensitive polymer and said therapeutic agent.

3. The formulation of claim 1, wherein the nanoparticles further comprise a component selected from the group consisting of a surfactant, a lipid, a mucoadhesive polymer, and a combination thereof.

4. The formulation of claim 1, wherein less than 5% of the therapeutic agent is released from the nanoparticles 2 hours after placing the nanoparticles in an aqueous medium at a pH of less than about 2.0.

5. The formulation of claim 1, wherein the nanoparticles have a mean particle size from about 10 nm to about 30 nm.

6. The formulation of claim 1, wherein the therapeutic agent is a peptide, a protein, a nucleic acid, a small molecule drug, or a combination thereof.

7. The formulation of claim 1, wherein the therapeutic agent is insulin.

8. An oral formulation of a therapeutic agent, the formulation comprising a plurality of nanoparticles, the nanoparticles comprising a pH-sensitive polymer and a therapeutic agent, and wherein the polymer is insoluble at acidic pH and soluble at neutral or alkaline pH, the pH-sensitive polymer is selected from the group consisting of a copolymer of methacrylic acid and an acrylic or methacrylic ester, methacrylic acid-methylmethacrylate copolymer, methacrylic acid-ethyl acrylate copolymer, a cellulose derivative, cellulose acetate phthalate, cellulose acetate succinate, cellulose acetate trimellitate, hydroxypropyl methylcellulose phthalate, hydroxypropyl methylcellulose acetate succinate, and combinations thereof, and the therapeutic agent has a molecular weight of more than 10000 Daltons; wherein a suspension of the nanoparticles is made by a process comprising dissolving the therapeutic agent and suspending the pH-sensitive polymer in an aqueous medium in which the therapeutic agent is soluble and associating the dissolved therapeutic agent and the suspended pH-sensitive polymer in the aqueous medium by adjusting the pH between about 5.5 and about 8 so as to form nanoparticles having a mean particle size of 100 nm or less with mixing alone and without the use of sonication, heat, or any other input of external energy; wherein the therapeutic agent and pH-sensitive polymer do not dissociate from the nanoparticles at acidic pH, with the proviso that the nanoparticles do not contain two different polymers, one polymer present in a core structure and the other polymer present in a shell structure and associated with the therapeutic agent.

9. The formulation of claim 8, wherein the nanoparticles consist essentially of said pH-sensitive polymer and said therapeutic agent.

10. The formulation of claim 8, wherein the nanoparticles further comprise a component selected from the group consisting of a surfactant, a lipid, a mucoadhesive polymer, and a combination thereof.

11. The formulation of claim 8, wherein less than 5% of the therapeutic agent is released from the nanoparticles 2 hours after placing the nanoparticles in an aqueous medium at a pH of less than about 2.0.

12. The formulation of claim 8, wherein the therapeutic agent is selected from the group consisting of a protein, a nucleic acid, an antibody, a virus-like particle, a vector, a vaccine, and a combination thereof.

13. The formulation of claim 12, wherein the therapeutic agent is an antibody selected from the group consisting of anti-EGFR, anti-Her2, anti-RSV, anti-interleukin, and anti-TNF, or selected from the group consisting of cetuximab, trastuzumab, palivizumab, tocilizumab, and adalimumab.

14. A method of preparing an orally administrable formulation of a therapeutic agent, the method comprising dissolving the therapeutic agent and suspending a pH-sensitive polymer in an aqueous medium in which the therapeutic agent is soluble and associating the dissolved therapeutic agent and the suspended pH-sensitive polymer in the aqueous medium by adjusting the pH between about 5.5 and about 8 so as to form nanoparticles with mixing alone and without the use of heat, sonication, or any other input of external energy; wherein the therapeutic agent has a molecular weight from about 1000 to about 10000 Daltons and the nanoparticles have a mean particle size of 50 nm or less, or wherein the therapeutic agent has a molecular weight from about 10000 to about 500000 Daltons and the nanoparticles have a mean particle size of 100 nm or less; wherein the therapeutic agent and pH-sensitive polymer do not dissociate from the nanoparticles at acidic pH; wherein the polymer is insoluble at acidic pH and soluble at neutral or alkaline pH, and wherein the pH-sensitive polymer is selected from the group consisting of a copolymer of methacrylic acid and an acrylic or methacrylic ester, methacrylic acid-methylmethacrylate copolymer, methacrylic acid-ethyl acrylate copolymer, a cellulose derivative, cellulose acetate phthalate, cellulose acetate succinate, cellulose acetate trimellitate, hydroxypropyl methylcellulose phthalate, hydroxypropyl methylcellulose acetate succinate, and combinations thereof;

wherein the method avoids the use of organic solvents, and wherein the nanoparticles do not contain two different polymers, one polymer present in a core structure and the other polymer present in a shell structure and associated with the therapeutic agent.

15. The method of claim 14, wherein the aqueous medium comprises a surfactant, a lipid, and a buffer.

16. The method of claim 15, wherein the aqueous medium comprises from 0 to 10 mM sodium taurocholate as the surfactant, 0 to 1.5 mM phosphatidylcholine as the lipid, 0 to 150 mM sodium chloride, and 0 to 50 mM sodium phosphate as the buffer.

17. The method of claim 14, further comprising:
lyophilizing the formulation.

18. The method of claim 14, wherein the therapeutic agent is selected from the group consisting of a peptide, a protein, a nucleic acid, an antibody, a vaccine, a vector, and a combination thereof.

19. An oral formulation of a therapeutic agent prepared by the method of claim 14.

20. The formulation of claim 1, wherein the therapeutic agent has a molecular weight from about 3000 to about 10000 Daltons.

21. The formulation of claim 1, wherein the therapeutic agent has a molecular weight from about 3000 to about 8000 Daltons.

22. The formulation of claim 1, wherein the pH-sensitive polymer is hydroxypropyl methylcellulose acetate succinate or methylmethacrylate/methacrylate copolymer.

23. The formulation of claim 9, wherein the pH-sensitive polymer is hydroxypropyl methylcellulose acetate succinate or methylmethacrylate/methacrylate copolymer.

24. The method of claim 14, wherein the pH-sensitive polymer is hydroxypropyl methylcellulose acetate succinate or a methylmethacrylate/methacrylate copolymer.

* * * * *